(12) United States Patent
Stradiotto

(10) Patent No.: US 10,322,410 B2
(45) Date of Patent: Jun. 18, 2019

(54) LIGAND FOR CATALYST OR PRE-CATALYST AND METHOD OF FORMING C(SP2)-N BOND

(71) Applicant: DALHOUSIE UNIVERSITY, Halifax (CA)

(72) Inventor: Mark John Stradiotto, Halifax (CA)

(73) Assignee: DALHOUSIE UNIVERSITY, Halifax (CA)

( * ) Notice: Subject to any disclaimer, the term of this patent is extended or adjusted under 35 U.S.C. 154(b) by 0 days.

(21) Appl. No.: 15/560,942

(22) PCT Filed: Jun. 1, 2016

(86) PCT No.: PCT/CA2016/050622
§ 371 (c)(1),
(2) Date: Sep. 22, 2017

(87) PCT Pub. No.: WO2016/191873
PCT Pub. Date: Dec. 8, 2016

(65) Prior Publication Data
US 2018/0141030 A1 May 24, 2018

Related U.S. Application Data

(60) Provisional application No. 62/171,370, filed on Jun. 5, 2015.

(51) Int. Cl.
| C07F 9/141 | (2006.01) |
| B01J 31/24 | (2006.01) |
| C07F 9/6571 | (2006.01) |
| C07C 209/10 | (2006.01) |
| C07C 209/18 | (2006.01) |

(Continued)

(52) U.S. Cl.
CPC .......... *B01J 31/2438* (2013.01); *B01J 31/28* (2013.01); *C07C 209/10* (2013.01); *C07C 209/18* (2013.01); *C07C 211/58* (2013.01); *C07C 213/02* (2013.01); *C07C 217/90* (2013.01); *C07C 217/92* (2013.01); *C07C 221/00* (2013.01); *C07C 225/22* (2013.01); *C07C 253/30* (2013.01); *C07F 9/657163* (2013.01);

(Continued)

(58) Field of Classification Search
None
See application file for complete search history.

(56) References Cited

U.S. PATENT DOCUMENTS

2010/0121092 A1  5/2010  Biel et al.

OTHER PUBLICATIONS

Fanjul et al. (Dalton Transactions, 42, 100-115 (Year: 2013).*

(Continued)

*Primary Examiner* — Yun Qian
(74) *Attorney, Agent, or Firm* — Borden Ladner Gervais LLP

(57) ABSTRACT

A compound having a chemical formula according to Formula (I) is disclosed where one of $Z_1$, $Z_2$ and $Z_3$ is and one of the $Z_1$, $Z_2$, and $Z_3$ that is bonded to a carbon atom that is adjacent to the carbon atom bonded to is $P(AR_1)(A'R_2)$. Metal-based catalyst and pre-catalysts, such as nickel-based catalysts and precatalysts, where the metal is complexed to the compound are also disclosed. Methods of forming C(sp2)-N bonds are also disclosed.

21 Claims, 9 Drawing Sheets

(51) Int. Cl.
| | |
|---|---|
| C07F 15/04 | (2006.01) |
| C07C 213/02 | (2006.01) |
| C07C 221/00 | (2006.01) |
| C07C 253/30 | (2006.01) |
| C07J 41/00 | (2006.01) |
| B01J 31/28 | (2006.01) |
| C07C 211/58 | (2006.01) |
| C07C 217/90 | (2006.01) |
| C07C 217/92 | (2006.01) |
| C07C 225/22 | (2006.01) |

(52) U.S. Cl.
CPC ............ *C07F 15/04* (2013.01); *C07F 15/045* (2013.01); *C07J 41/0011* (2013.01)

(56) References Cited

OTHER PUBLICATIONS

Adjabeng et al., "Novel Class of Tertiary Phosphine Ligands Based on a Phospha-adamantane Framework and Use in the Suzuki Cross-Coupling Reactions of Aryl Halides under Mild Conditions," Organic Letters, Mar. 2003, vol. 5 (6), pp. 953-955.
Albaneze-Walker et al., "Imidazolylsulfonates: Electrophilic Partners in Cross-Coupling Reactions," Organic Letters, Apr. 2009, vol. 11 (7), pp. 1463-1466.
Alsabeh et al., "Addressing Challenges in Palladium-Catalyzed Cross-Couplings of Aryl Mesylates: Monoarylation of Ketones and Primary Alkyl Amines," Angewandte Chemie, Jul. 2013, vol. 52 (28), pp. 7242-7246.
Ananikov, "Nickel: The "Spirited Horse" of Transition Metal Catalysis," ACS Catalysis, 2015, vol. 5 (3), pp. 1964-1971.
Baker et al., "Microbial Degradation of Methanesulphonic Acid: A Missing Link in the Biogeochemical Sulphur Cycle," Nature , Apr. 1991, vol. 350, pp. 627-628.
Borzenko et al., "Nickel-Catalyzed Monoarylation of Ammonia," Angewandte Chemie, Mar. 2015, vol. 54 (12), pp. 3773-3777.
Busacca et al., "The Growing Impact of Catalysis in the Pharmaceutical Industry," Advanced Synthesis & Catalysis, Aug. 2011, vol. 353 (11-12), pp. 1825-1864.
Camasso et al., "Design, Synthesis, and Carbon-Heteroatom Coupling Reactions of Organometallic Nickel(IV) Complexes," Science, Mar. 2015, vol. 347 (6227), pp. 1218-1220.
Cheung et al., "Mild and Highly Selective Palladium-Catalyzed Monoarylation of Ammonia Enabled by the Use of Bulky Biarylphosphine Ligands and Palladacycle Precatalysts," Organic Letters, Jul. 2013, vol. 15 (14), pp. 3734-3737.
Christmann et al., "Monoligated Palladium Species as Catalysts in Cross-Coupling Reactions," Angewandte Chemie, Jan. 2005, vol. 44 (3), pp. 366-374.
Cooper et al., "Factors Determining the Selection of Organic Reactions by Medicinal Chemists and the Use of These Reactions in Arrays (Small Focused Libraries)," Angewandte Chemie, Oct. 2010, vol. 49 (44), pp. 8082-8091.
Crawford et al., "BippyPhos: A Single Ligand with Unprecedented Scope in the Buchwald-Hartwig Amination of (Hetero)aryl Chlorides," Chemistry , Dec. 2013, vol. 19 (49), pp. 16760-16771.
Creutz et al., "Photoinduced Ullmann C—N Coupling: Demonstrating the Viability of a Radical Pathway," Science, Nov. 2012, vol. 338 (6107), pp. 647-651.
Dr. Max Appl., "Ammonia: Principles and Industrial Practice," Wiley Online Library, Wiley-VCH, Jan. 1999.
Du et al., "Selective N-Alkylation of Amines with Alcohols by Using Non-Metal-Based Acid-Base Cooperative Catalysis," Chemistry, Oct. 2011, vol. 17 (44), pp. 12262-12267.
Fan et al., "Assembly of Primary (Hetero)Arylamines via CuI/Oxalic Diamide-Catalyzed Coupling of Aryl Chlorides and Ammonia," Organic Letters, 2015, vol. 17 (23), pp. 5934-5937.

Fine Nathel et al., "Nickel-Catalyzed Amination of Aryl Chlorides and Sulfamates in 2-Methyl-THF," ACS Catalysis, Sep. 2014, vol. 4 (9), pp. 3289-3293.
Gao et al., "Nickel-Catalyzed Cross-Coupling of Diarylamines with Haloarenes," Organic & Biomolecular Chemistry, 2009, vol. 7, pp. 3922-3925.
Ge et al., "Controlling First-Row Catalysts: Amination of Aryl and Heteroaryl Chlorides and Bromides with Primary Aliphatic Amines Catalyzed by a BINAP-Ligated Single-Component Ni(0) Complex," Journal of the American Chemical Society, Jan. 2014, vol. 136 (4), pp. 1617-1627.
Gerristma et al., "Phospha-Adamantanes as Ligands for Organopalladium Chemistry: Aminations of Aryl Halides," Tetrahedron Letters, Nov. 2004, vol. 45 (45), pp. 8319-8321.
Green et al., "Nickel-Catalyzed Amination of Aryl Chlorides with Ammonia or Ammonium Salts," Angewandte Chemie, Mar. 2015, vol. 54 (12), pp. 3768-3772.
Green et al., "Palladium-Catalyzed Amination of Aryl Chlorides and Bromides with Ammonium Salts," Organic Letters, Sep. 2014, vol. 16 (17), pp. 4388-4391.
Grushin et al., "Transformations of Chloroarenes, Catalyzed by Transition-Metal Complexes," Chemical Reviews, 1994, vol. 94 (4), pp. 1047-1062.
Guram et al., "A Simple Catalytic Method for the Conversion of Aryl Bromides to Arylamines," Angewandte Chemie, 1995, vol. 34 (12), pp. 1348-1350.
Hartwig, "Evolution of a Fourth Generation Catalyst for the Amination and Thioetherification of Aryl Halides," Accounts of Chemical Research, Nov. 2008, vol. 41 (11), pp. 1534-1544.
Hidai et al., "Oxidative Additions to Nickel(0): Preparation and Properties of a New Series of Arylnuckel(II) Complexes," Journal of Organometallic Chemistry, Jul. 1971, vol. 30 (2), pp. 279-282.
Iglesias et al., "Synthesis, Structural Characterization, and Catalytic Activity of IPrNi(styrene)2 in the Amination of Aryl Tosylates," Organometallics, Sep. 2012, vol. 31 (17), pp. 6312-6316.
International Patent Application No. PCT/CA2016/050622, International Preliminary Search Report dated Dec. 5, 2017.
International Patent Application No. PCT/CA2016/050622, International Search Report and Written Opinion dated Sep. 12, 2016.
Jana et al., "Advances in Transition Metal (Pd,Ni,Fe)-Catalyzed Cross-Coupling Reactions Using Alkyl-Organometallics as Reaction Partners," Chemical Reviews, 2011, vol. 111 (3), pp. 1417-1492.
Joshaghani et al., "Highly Efficient Suzuki Coupling Using Moderately Bulky Tolylphosphine Ligands," Journal of Molecular Catalysis A: Chemical, Aug. 2007, vol. 273 (1-2), pp. 310-315.
Kitov et al., "Rapid, Hydrolytically Stable Modification of Aldehyde-Terminated Proteins and Phage Libraries," Journal of the American Chemical Society, 2014, vol. 136 (23), pp. 8149-8152.
Klinkenberg et al., "Catalytic Organometallic Reactions of Ammonia," Angewandte Chemie, Jan. 2011, vol. 50 (1), pp. 86-95.
Lemen et al., "Palladium-Catalyzed sp2 C—N Bond Forming Reactions: Recent Developments and Applications," Topics in Organometallic Chemistry, Feb. 2013, vol. 46, pp. 1-54.
Lewis et al., "Metal-Free Functionalization of N,N-Dialkylanilines via Temporary Oxidation to N,N-Dialkylaniline N-Oxides and Group Transfer," Organic Letters, Jul. 2014, vol. 16 (14), pp. 3832-3835.
Li et al., "Synthesis, Structure, and Catalytic Behavior of a PSiP Pincer-Type Iridium(III) Complex," Inorganic Chemistry Communications, Aug. 2011, vol. 14 (8), pp. 1306-1310.
Littke et al., "Palladium-Catalyzed Coupling Reactions of Aryl Chlorides," Angewandte Chemie, Nov. 2002, vol. 41 (22), pp. 4176-4211.
Liu et al., "Highly Enantioselective Synthesis of Chiral Secondary Amines by Gold(I)/ Chiral Brønsted Acid Catalyzed Tandem Intermolecular Hydroamination and Transfer Hydrogenation Reactions," Organic Letters, 2009, vol. 11 (18), pp. 4204-4207.
Lou et al., "The Acute Hepatotoxicity of Tacrine Explained by 1H NMR Based Metabolomic Profiling," Toxicology Research, Jul. 2015, vol. 4, pp. 1465-1478.

(56) References Cited

OTHER PUBLICATIONS

Louie et al., "Palladium-Catalyzed Synthesis of Arylamines from Aryl Halides. Mechanistic Studies Lead to Coupling in the Absence of Tin Reagents," Tetrahedron Letters, May 1995, vol. 36 (21), pp. 3609-3612.

Lundgren et al., "A P,N-Ligand for Palladium-Catalyzed Ammonia Arylation: Coupling of Deactivated Aryl Chlorides, Chemoselective Arylations, and Room Temperature Reactions," Angewandte Chemie, Jun. 2010, vol. 49 (24), pp. 4071-4074.

Manolikakes et al., "An Efficient Silane-Promoted Nickel-Catalyzed Amination of Aryl and Heteroaryl Chlorides," Journal of Organic Chemistry, Jan. 2008, vol. 73 (4), pp. 1429-1434.

Martin et al., "Efficient C—N and C—S Bond Formation Using the Highly Active [Ni(allyl)Cl(IPr*OMe)] Precatalyst," European Journal of Organic Chemistry, 2014, vol. 2014 (15), pp. 3127-3131.

Mesganaw et al., "Ni- and Fe-Catalyzed Cross-Coupling Reactions of Phenol Derivatives," Organic Process Reserarch & Development, 2013, vol. 17 (1), pp. 29-39.

Mesganaw et al., "Nickel-catalyzed Amination of Aryl Carbamates and Sequential Site-Selective Cross-Coupling," Chemical Science, 2011, vol. 2, pp. 1766-1771.

Mikhel et al., "Cage Phosphinites: Ligands for Efficient Nickel-Catalyzed Hydrocyanation of 3-Pentenenitrile," Organometallics, Feb. 2011, vol. 30 (5), pp. 947-985.

Monnier et al., "Copper-Catalyzed C(aryl)-N Bond Formation," Topics in Organometallic Chemistry, Oct. 2013, vol. 46, pp. 173-204.

Morvillo et al., "Reactions of Organic Halides and Cyanides with Bis(Tricyclohexylphospine)nickel(0)," Journal of Organometallic Chemistry, Mar. 1981, vol. 208 (1), pp. 103-113.

Park et al., "Development of an Air-Stable Nickel Precatalyst for the Amination of Aryl Chlorides, Sulfamates, Mesylates, and Triflates," Organic Letters, Jan. 2014, vol. 16 (1), pp. 220-223.

Pringle et al., "Phosphatrioxa-Adamantane Ligands," Phosphorus(III) Ligands in Homogeneous Catalysis: Design and Synthesis, First Edition, 2012, pp. 391-404.

Rosen et al., "Nickel-Catalyzed Cross-Couplings Involving Carbon-Oxygen Bonds," Chemical Reviews, Mar. 2011, vol. 111 (3), pp. 1346-1416.

Roughley et al., "The Medicinal Chemist's Toolbox: An Analysis of Reactions Used in the Pursuit of Drug Candidates," Journal of Medicinal Chemistry, 2011, vol. 54 (10), pp. 3451-3479.

Rull et al., "C—N Coupling of Indoles and Carbazoles with Aromatic Chlorides Catalyzed by a Single-Component NHC-Nickel(O) Precursor," Advanced Synthesis & Catalysis, 2015, vol. 357, pp. 907-911.

Schon et al., "An Improved Synthesis of 3 Aminoestrone," Tetrahedron Letters, Oct. 2005, vol. 46 (42), pp. 7111-7115.

Shen et al., "Highly Reactive, General and Long-Lived Catalysts for Palladium-Catalyzed Amination of Heteroaryl and Aryl Chlorides, Bromides, and Iodides: Scope and Structure-Activity Relationships," Journal of the American Chemical Society, May 2008, vol. 130 (20), pp. 6586-6596.

Shen et al., "Palladium-Catalyzed Coupling of Ammonia and Lithium Amide with Aryl Halides," Journal of the American Chemical Society, 2006, vol. 128 (31), pp. 10028-10029.

Standley et al., "A Broadly Applicable Strategy for Entry into Homogeneous Nickel(0) Catalysts from Air-Stable Nickel(II) Complexes," Organometallics, Apr. 2014, vol. 33 (8), pp. 2012-2018.

Standley et al., "Simplifying Nickel(0) Catalysis: An Air-Stable Nickel Precatalyst for the Internally Selective Benzylation of Terminal Alkenes," Journal of the American Chemical Society, Jan. 2013, vol. 135 (4), pp. 1585-1592.

Stradiotto., "Ancillary Ligand Design in the Development of Palladium Catalysts for Challenging Selective Monoarylation Reactions," Chapter 5, RSC Catalysis Series No. 21, New Trends in Cross-Coupling: Theory and Applications, 2014, pp. 226-251.

Surry et al., "Biaryl Phosphane Ligands in Palladium-Catalyzed Amination," Angewandte Chemie, 2008, vol. 47 (34), pp. 6338-6361.

Tardiff et al., "Rational and Predictable Chemoselective Synthesis of Oligoamines via Buchwald-Hartwig Amination of (Hetero)Aryl Chlorides Employing Mor-DalPhos," Journal of Organic Chemistry, 2012, vol. 77 (2), pp. 1056-1071.

Tasker et al., "Highly Regioselective Indoline Synthesis under Nickel/Photoredox Dual Catalysis," Journal of the American Chemical Society, Aug. 2015, vol. 137 (30), pp. 9531-9534.

Tasker et al., "Recent advances in homogeneous nickel catalysis," Nature, May 2014, vol. 509 (7500), pp. 299-309.

Teguh et al., "Novel Conjugated Quinoline-Indoles Compromise Plasmodium falciparum Mitochondrial Function and Show Promising Antimalarial Activity," Journal of Medicinal Chemistry, Aug. 2013, vol. 56 (15), pp. 6200-6215.

Vo et al., "Palladium-Catalyzed Coupling of Ammonia with Aryl Chlorides, Bromides, Iodides, and Sulfonates: A General Method for the Preparation of Primary Arylamines," Journal of the American Chemical Society, Jul. 2009, vol. 131 (31), pp. 11049-11061.

Voth et al., "Transition-Metal-Free Access to Primary Anilines from Boronic Acids and a Common +NH2 Equivalent," The Journal of Organic Chemistry, Jan. 2015, vol. 80 (5), pp. 2545-2553.

Wagaw et al., "Palladium-Catalyzed Coupling of Optically Active Amines with Aryl Bromides," Journal of the American Chemical Society, Sep. 1997, vol. 119 (36), pp. 8451-8458.

Wilkinson, "Greener" Friedel-crafts Acylations: A Metal- and Halogen-Free Methodology, Organic Letters, May 2011, vol. 13 (9), pp. 2232-2235.

Wolfe et al., "Nickel-Catalyzed Amination of Aryl Chlorides," Journal of the American Chemical Society, 1997, vol. 119 (26), pp. 6054-6058.

Yang et al., "Synthesis of Dibenzo[b,f][1,4]Oxazepin-11(10H)-Ones via Intramolecular Cyclocarbonylation Reactions Using Pdl2/Cytop 292 as the Catalytic System," Journal of Organometallic Chemistry, 2010, vol. 75 (18), pp. 6297-6299.

Zhang et al., "Skeleton Decoration of NHCs by Amino Groups and its Sequential Booster Effect on the Palladium-a-Catalyzed Buchwald-Hartwig Amination," Angewandte Chemie, Jun. 2014, vol. 53 (25), pp. 6482-6486.

Zhou et al., "CuI/Oxalic Diamide Catalyzed Coupling Reaction of (Hetero)Aryl Chlorides and Amines," Journal of the American Chemical Society, Sep. 2015, vol. 137 (37), pp. 11942-11945.

Zhou et al., "Highly Efficient Ligands for the Palladium-Assisted Double N-Arylation of Primary Amines for One-Sep construction of Carbazoles," Advanced Synthesis & Catalysis, Mar. 2010, vol. 352, pp. 616-620.

\* cited by examiner

LIGAND FOR CATALYST OR PRE-CATALYST AND METHOD OF FORMING C(SP2)-N BOND

CROSS-REFERENCE TO RELATED APPLICATIONS

This application claims the benefit of U.S. provisional application Ser. No. 62/171,370, filed Jun. 5, 2015. This application is incorporated by reference.

FIELD

The present disclosure relates to ligands for catalysts or pre-catalysts which may be used to form C(sp2)-N bonds.

BACKGROUND

The following paragraphs are not an admission that anything discussed in them is prior art or part of the knowledge of persons skilled in the art.

Bond-forming reactions are of widespread interest to synthetic chemists, especially those cross-coupling reactions that create new C—C, C—N, C—O, C—S, and C—P bonds. These reactions rely upon catalysts to improve the speed and yield of reaction. C—N cross-coupling is of particular significance in the pharmaceutical industry.

The palladium-catalyzed arylation of amines and related NH-containing substrates using (hetero)aryl (pseudo)halide coupling partners (i.e. Buchwald-Hartwig amination, BHA) has emerged as a method for the construction of C(sp2)-N bonds that is widely employed in the synthesis of pharmaceuticals, natural products, and functional materials on both benchtop and industrial scales.

In the early development of BHA, simple triarylphosphines were used as supporting ancillary ligands. However, in the ensuing years, it is now understood that ancillary ligands must be chosen so as to promote the formation of a monoligated, electron-rich Pd(0) complex that is activated towards (hetero)aryl (pseudo)halide oxidative addition, while also enabling C—N bond reductive elimination to afford the (hetero)aryl amine product. The steric demands of these two key mechanistic steps suggest the application of bulky ancillary ligands, to favor low-coordination and to encourage reductive elimination. However, the ancillary ligand electronic requirements for oxidative addition and reductive elimination are orthogonal, with strongly electron-donating ligands favoring oxidative addition, and less electron-donating ligands favoring reductive elimination. This has made selection of such ligands difficult.

Electron-rich ligands have in general proven to be most effective, especially in combination with substrates for which oxidative addition is challenging (e.g. less expensive and more abundant, but less reactive aryl chlorides). On the basis of these guiding principles, several diverse classes of bulky, electron-rich ancillary ligands have emerged for use in BHA, including: trialkylphosphines (e.g., cataCXium A); (hetero)biaryl monophosphines (e.g., Buchwald ligands, BippyPhos); bisphosphines (e.g., JosiPhos CyPF-tBu); P,N-ligands (e.g., Mor-DalPhos); and N-heterocyclic carbenes (e.g., IPr, IPent, and others). From a practical perspective, all of the above are commercially available and air-stable as the free-ligand or in pre-catalysts form, thus facilitating uptake by synthetic chemists. The development and application of these and other ancillary ligand families has enabled broad substrate scope in BHA chemistry, including challenging and diverse transformations ranging from the selective monoarylation of basic and nucleophilic species (e.g. ammonia and primary alkylamines) to the arylation of comparatively acidic substrates (e.g. amides and NH heterocycles). While some particularly versatile ancillary ligands have been identified, in most cases the selection of a strategically optimized ancillary ligand is required in order to achieve ideal results for a given substrate class in BHA.

Introduction

The following introduction is intended to introduce the reader to this specification but not to define any invention. One or more inventions may reside in a combination or sub-combination of the elements or steps described below or in other parts of this document. The inventors do not waive or disclaim their rights to any invention or inventions disclosed in this specification merely by not describing such other invention or inventions in the claims.

Notwithstanding the broad utility of BHA protocols, the expense and relatively low abundance of palladium, and the often costly nature of the required ancillary ligands, provide impetus for the development of first-row transition metal catalysts for C—N cross-couplings. The authors of the present disclosure believe that the smaller size and distinct electronic properties of the 3d metals, relative to palladium, may provide access to new and useful reactivity manifolds. Among first-row metals, copper-based catalysts have a particularly long-standing history in C—N cross-coupling chemistry. Unfortunately, copper-based catalysts reported to date for C—N cross-couplings have proven incapable of effecting transformations of low cost and wide availability (hetero)aryl chlorides or sulfonates.

The authors of the present disclosure believe that nickel catalysis offers promise as a competitive alternative to BHA protocols. It is significantly less expensive than palladium (e.g. in terms of the cost of simple $MX_2$ salts, $NiCl_2 < 1\$/g$; $PdCl_2 > \$50/g$). Conventional phosphine ancillary ligands employed in the early development of both BHA and related nickel-catalyzed reactions, including $PPh_3$, rac-BINAP, and DPPF, are useful in some circumstances but have not been generally applicable. Ammonia monoarylation has been reported with the use of nickel complexes containing Josi-Phos, however JosiPhos is an expensive, fullerene-containing reagent.

There remains a need to develop chemical catalysts which may be used to form C(sp2)-N bonds.

In some embodiments, the present disclosure provides a ligand for a catalyst or pre-catalyst. The catalyst or pre-catalyst may be a nickel-based catalyst or pre-catalyst. The ligand for the catalyst or pre-catalyst according to the present disclosure has a chemical formula as illustrated in Formula (I):

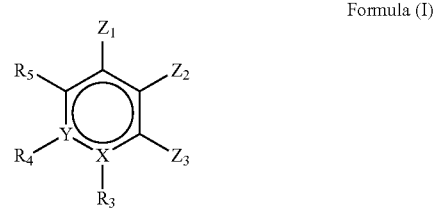

Formula (I)

In a ligand according to Formula (I):
X is C, N, O or S;
Y is C or a bond;

one of $Z_1$, $Z_2$ and $Z_3$ is

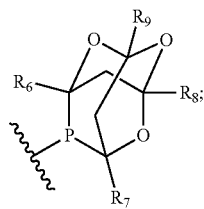

when $Z_1$ is

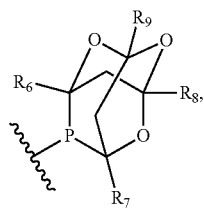

then $Z_2$ is $P(AR_1)(A'R_2)$, and $Z_3$ is H, alkyl, alkoxy, thioalkoxy, carboxy, carboxyalkyl, or halogen;

when $Z_2$ is

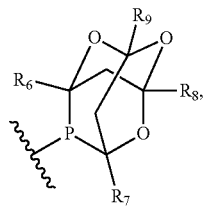

then one of $Z_1$ and $Z_3$ is $P(AR_1)(A'R_2)$, and the other of $Z_1$ and $Z_3$ is H, alkyl, alkoxy, thioalkoxy, carboxy, carboxyalkyl, or halogen; and when $Z_3$ is

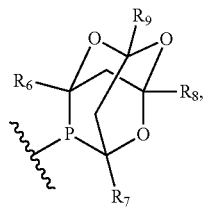

then $Z_2$ is $P(AR_1)(A'R_2)$, and $Z_1$ is H, alkyl, alkoxy, thioalkoxy, carboxy, carboxyalkyl, or halogen;

A and A' are, independently: O or a bond;

$R_1$ and $R_2$ are, independently: aryl, alkyl, or cycloalkyl, where the aryl, alkyl or cycloalkyl is substituted or unsubstituted;

when X is C, then Y is C, and $R_3$ and $R_4$ are, independently: H, alkyl, alkoxy, thioalkoxy, carboxy, carboxyalkyl, or halogen;

when X is N and when Y is a C, then $R_3$ is absent and $R_4$ is: H, alkyl, alkoxy, thioalkoxy, carboxy, carboxyalkyl, or halogen;

when X is N and when Y is a bond, then $R_4$ is absent and $R_3$ is: H, aryl, or alkyl;

when X is O or S, then Y is a bond, and $R_3$ and $R_4$ are both absent;

$R_5$ is: H, alkyl, alkoxy, thioalkoxy, carboxy, carboxyalkyl, or halogen; and $R_6$, $R_7$, $R_8$, and $R_9$ are, independently, alkyl.

In other embodiments, the present disclosure provides a nickel-based catalyst or pre-catalyst that includes nickel complexed to a ligand according to the present disclosure.

In other embodiments, the present disclosure provides a method of forming a C(sp2)-N bond by reacting an aryl halide, a heteroaryl halide, an aryl pseudohalide, or a heteroaryl pseudohalide, with an amine-containing compound in the presence of a catalytically effective quantity of a nickel-based catalyst or pre-catalyst according to the present disclosure.

BRIEF DESCRIPTION OF THE DRAWINGS

Embodiments of the present disclosure will now be described, by way of example only, with reference to the attached Figures.

DETAILED DESCRIPTION

Figure 1:
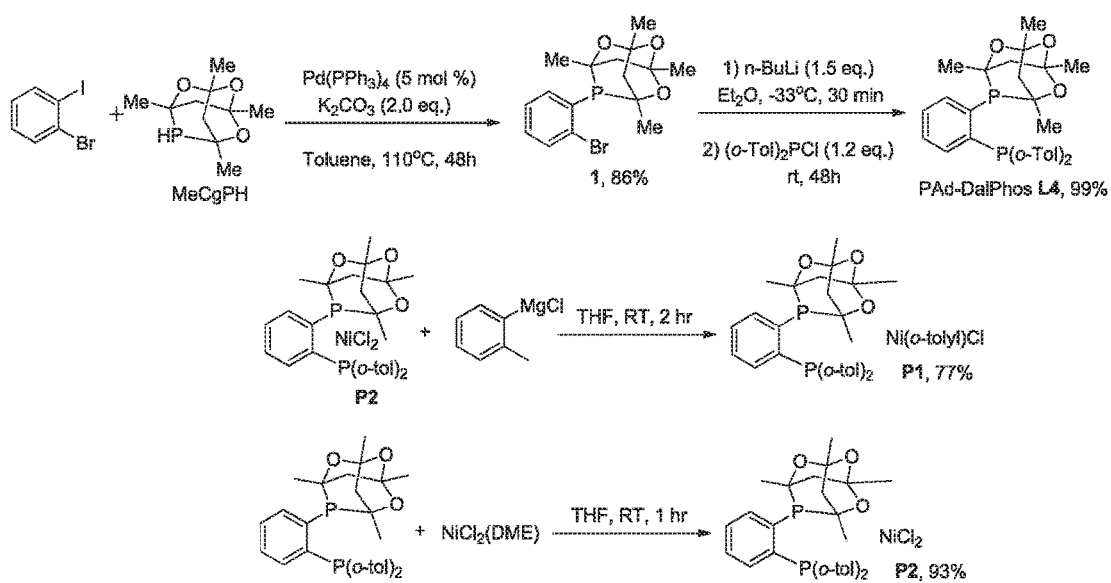
FIG. 1 is an illustration of a synthetic scheme which may be used to produce nickel-based pre-catalysts according to the present disclosure.

Generally, the present disclosure provides a ligand for a catalyst or pre-catalyst where the ligand has a chemical formula as illustrated in Formula (I):

Formula (I)

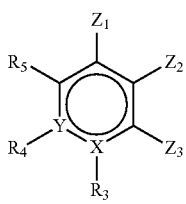

In a ligand according to Formula (I):

X is C, N, O or S;

Y is C or a bond;

when X is C, then Y is C, and $R_3$ and $R_4$ are, independently: H, alkyl, alkoxy, thioalkoxy, carboxy, carboxyalkyl, or halogen;

when X is N and when Y is a C, then $R_3$ is absent and $R_4$ is: H, alkyl, alkoxy, thioalkoxy, carboxy, carboxyalkyl, or halogen;

when X is N and when Y is a bond, then $R_4$ is absent and $R_3$ is: H, aryl, or alkyl; and when X is O or S, then Y is a bond, and $R_3$ and $R_4$ are both absent;

one of $Z_1$, $Z_2$ and $Z_3$ is

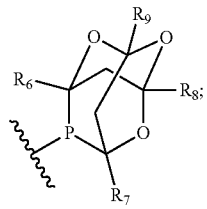

when $Z_1$ is

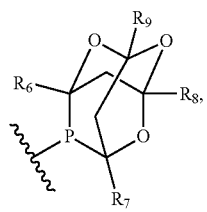

then $Z_2$ is $P(AR_1)(A'R_2)$, and $Z_3$ is H, alkyl, alkoxy, thioalkoxy, carboxy, carboxyalkyl, or halogen;

when $Z_2$ is

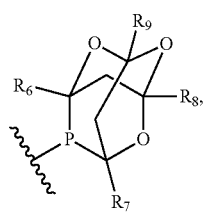

then one of $Z_1$ and $Z_3$ is $P(AR_1)(A'R_2)$, and the other of $Z_1$ and $Z_3$ is H, alkyl, alkoxy, thioalkoxy, carboxy, carboxyalkyl, or halogen; and when $Z_3$ is

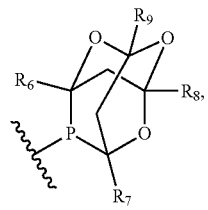

then $Z_2$ is $P(AR_1)(A'R_2)$, and $Z_1$ is H, alkyl, alkoxy, thioalkoxy, carboxy, carboxyalkyl, or halogen;

A and A' are, independently: O or a bond;

$R_1$ and $R_2$ are, independently: aryl, alkyl, or cycloalkyl, where the aryl, alkyl or cycloalkyl is substituted or unsubstituted;

$R_5$ is: H, alkyl, alkoxy, thioalkoxy, carboxy, carboxyalkyl, or halogen; and $R_6$, $R_7$, $R_8$, and $R_9$ are, independently, alkyl.

In some examples of a ligand according to Formula (I), the ligand has a chemical formula as illustrated in Formula (II):

Formula (II)

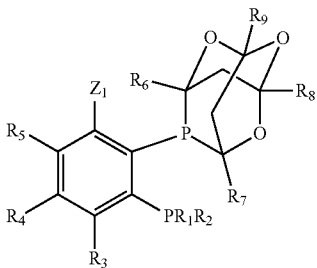

In a ligand according to Formula (II): X is C; Y is C; $Z_2$ is

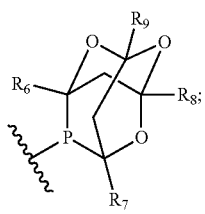

$Z_3$ is $P(AR_1)(A'R_2)$ where A and A' are bonds; and the remaining groups are as defined above.

In other examples of a ligand according to Formula (I), the ligand has a chemical formula as illustrated in Formula (III):

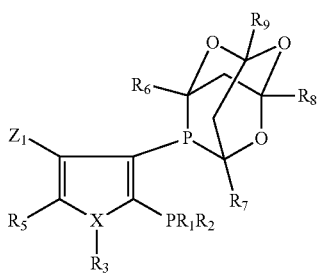

Formula (III)

In a ligand according to Formula (III): X is N, O or S; Y is a bond; $R_4$ is absent; $Z_2$ is

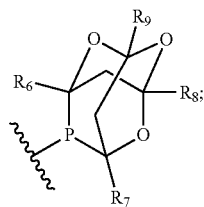

$Z_3$ is $P(AR_1)(A'R_2)$ where A and A' are bonds; and the remaining groups are as defined above.

In still other examples of a ligand according to Formula (I), the ligand has a chemical formula as illustrated in Formula (IV):

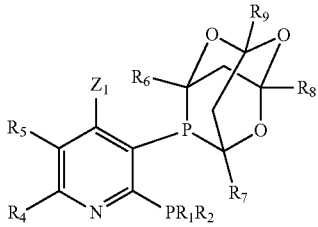

Formula (IV)

In a ligand according to Formula (IV): X is N; Y is C; $Z_2$ is

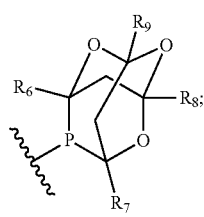

$Z_3$ is $P(AR_1)(A'R_2)$ where A and A' are bonds; and the remaining groups are as defined above.

In preferred examples of compounds according to Formulas (I) to (IV): X is C or N; $Z_1$ is H; $Z_2$ is

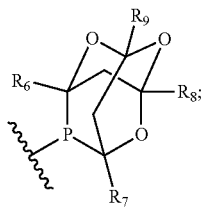

$Z_3$ is $P(AR_1)(A'R_2)$ where A and A' are bonds; $R_1$ and $R_2$ are, independently: tolyl (such as o-tolyl), phenyl, isopropyl, cyclohexyl, or tert-butyl, or 1-adamantyl; $R_3$ and $R_4$ are, independently: H or absent; $R_5$ is H; and $R_6$-$R_9$ are methyl.

Particular examples of ligands according to Formula (I) include ligands where X and Y are C; $Z_1$ is H; $Z_2$ is

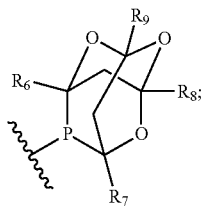

$Z_3$ is $P(AR_1)(A'R_2)$; A and A' are bonds; $R_3$-$R_5$ are H; $R_6$-$R_9$ are methyl; and $R_1$ and $R_2$ are: tolyl (such as o-tolyl), phenyl, iso-propyl, cyclohexyl, tert-butyl, or 1-adamantyl.

One particular example of a ligand according to Formula (I) has a chemical formula as illustrated in Formula (V):

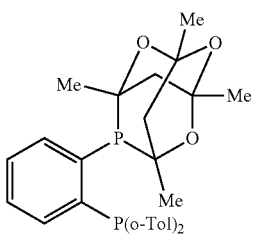

Formula (V)

The compound of Formula (V) is ortho-di(o-tolyl)phosphine functionalized 1,3,5,7-tetramethyl-2,4,8-trioxa-6-phenyl-6-phosphaadamantane.

Another particular example of a ligand according to Formula (I) has a chemical formula as illustrated in Formula (VI):

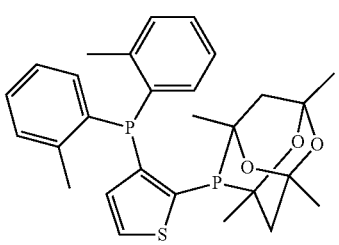

Formula (VI)

In a ligand according to Formula (VI): X is S; Y is a bond; $R_3$ and $R_4$ are absent; $R_5$ is H; $Z_1$ is H; $Z_2$ is $P(AR_1)(A'R_2)$ where A and A' are bonds and $R_1$ and $R_2$ are o-tolyl; and $Z_3$ is

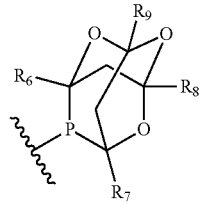

where $R_6$-$R_9$ are methyl.

In yet another particular example of a ligand according to Formula (I), the ligand has a chemical formula as illustrated in Formula (VII):

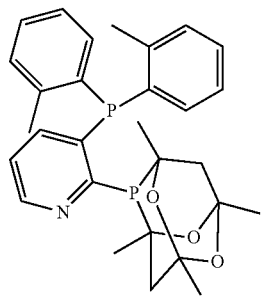

Formula (VII)

In a ligand according to Formula (VII): X is N; Y is a C; $R_3$ is absent; $R_4$ and $R_5$ are H; $Z_1$ is H; $Z_2$ is $P(AR_1)(A'R_2)$ where A and A' are bonds and $R_1$ and $R_2$ are o-tolyl; and $Z_3$ is

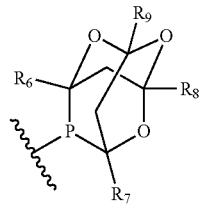

where $R_6$-$R_9$ are methyl.

The present disclosure also provides a nickel-based catalyst or pre-catalyst that includes nickel complexed to a ligand according to the present disclosure. The nickel may additionally be complexed to: two chloro groups; an o-tolyl group and a chloro group; two o-tolyl groups; two naphthyl groups; or one 1,5-cyclooctadiene (COD) groups. Preferred nickel-based catalysts or pre-catalysts according to the present disclosure include catalysts or pre-catalysts having a chemical formula as illustrated in Formula (VIII) and (IX):

Formula (VIII)

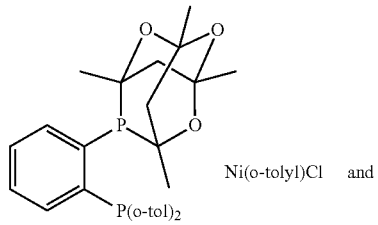

and

Formula (IX)

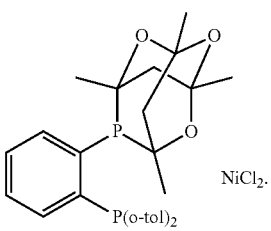

Other nickel-based catalysts or pre-catalysts according to the present disclosure include catalysts or pre-catalysts having a chemical formula as illustrated in Formula (X) to (XV):

Formula (X)

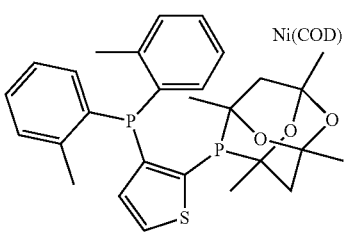

Formula (XI)

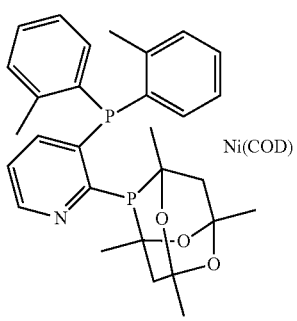

Formula (XII)

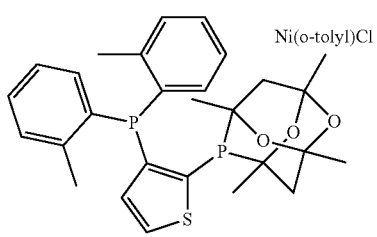

Formula (XIII)

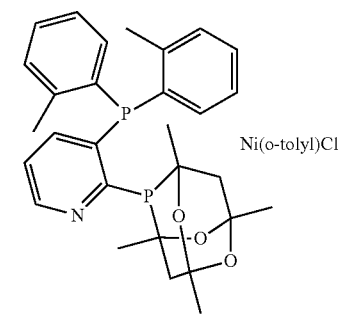

Formula (XIV)

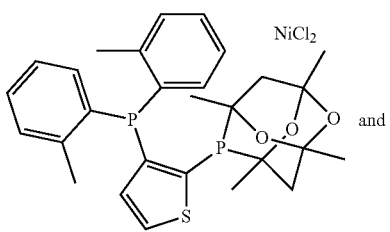

and

Formula (XV)

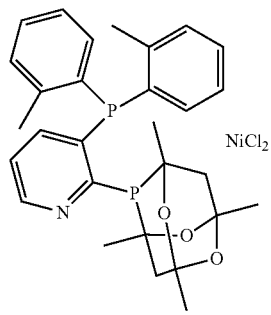

In the context of the present disclosure, a catalyst would be understood to refer to a chemical compound that increases the rate of a reaction without itself undergoing any permanent chemical change. A pre-catalyst would be understood to refer to a chemical compound that is converted into a catalyst in situ when subjected to the reaction conditions. The compounds of Formula (VIII) to (XI) are examples of pre-catalysts according to the present disclosure. A compound of Formula (VIII) is naturally reduced to the required Ni(0) species under C—N cross-coupling conditions according to the present disclosure, while the compound of Formula (IX) requires an external reductant. Compounds of Formulas (VIII) and (IX) are both air-stable.

Without wishing to be bound by theory, the authors of the present disclosure believe that ligands that include two sterically demanding and relatively electron-poor phosphorus donor fragments gives rise to nickel catalysts which may be used for C—N cross-coupling reactions. The compound of Formula (V) is one example of a ligand with two sterically demanding and relatively electron-poor phosphorus donor fragments.

The present disclosure also provides a method of forming a C(sp2)-N bond by reacting an aryl halide, a heteroaryl halide, an aryl pseudohalide, or a heteroaryl pseudohalide with an amine-containing compound in the presence of a catalytically effective quantity of a nickel-based catalyst or pre-catalyst according to the present disclosure. The two reactive groups may be a part of the same molecule. That is, the aryl halide, heteroaryl halide, aryl pseudohalide, or heteroaryl pseudohalide may be chemically linked to the amine-containing compound before the C(sp2)-N bond is formed.

A catalytically effective quantity of the nickel-based catalyst or pre-catalyst may be at least 0.1 mol %, based on the number of moles of the aryl halide, the heteroaryl halide, the aryl pseudohalide, or the heteroaryl pseudohalide. In some examples, the catalytically effective quantity of the nickel-based catalyst or pre-catalyst may be from about 0.1 mol % to about 5 mol %.

The reagents may be dissolved in a solvent, such as toluene, or the reaction may be performed without solvent.

The reagents may be heated in a closed vessel. For example, the reagents may be sealed in a closed vessel and heated using a microwave reactor.

The halide acts as a leaving group in the catalyzed cross-coupling reaction. The halide is preferably Cl, Br or I. A pseudohalide would be understood to refer to a chemical group that could act as a leaving group in the catalyzed cross-coupling reaction. Exemplary pseudohalide groups include: cyano, isocyano, thiocyano, azido, —O-tosyl ("—OTs"), —O—$SO_2CF_3$ ("—OTf"), —O—$SO_2CH_3$ ("—OMs"), and —$OSO_2$-1H-imidazole ("imidazolyl$SO_3$,").

The aryl halide, heteroaryl halide, aryl pseudohalide, or heteroaryl pseudohalide may be electron-rich or electron-poor.

The amine-containing compound may be ammonia, a primary amine, or a secondary amine. The amine may be an aliphatic amine, an aromatic amine, or a heterocyclic secondary amine. More preferably, the amine may be a primary aliphatic amine, a primary aryl amine, a primary heteroaryl amine, or dimethylamine. Examples of an aliphatic amine include: $CH_3$—$NH_2$; $CH_3CH_2$—$NH_2$; $C_8H_{17}$—$NH_2$; sec-butylamine; and furfurylamine. Examples of a primary aryl amine include: analine; p-methylaniline; and p-methoxyaniline. Examples of a heterocyclic secondary amine include: 1H-indole.

The ammonia may be gaseous or in solution. The ammonia may be ammonium acetate. The solution may be 1,4-dioxane.

The method may include reacting the aryl halide, the heteroaryl halide, the aryl pseudohalide, or the heteroaryl pseudohalide, with the amine-containing compound in the presence of a base. The base may be sodium tert-butoxide or potassium tert-butoxide.

Methods according to the present disclosure may include heating the reaction mixture, such as to a temperature of at least 60° C., and preferably to a temperature of between about 100° C. to about 110° C.

Definitions

Unless otherwise defined, terms as used in the specification refer to the following definitions, as detailed below.

The term "alkyl" as used herein means a straight or branched chain hydrocarbon containing from 1 to 20 carbon atoms, preferably from 1 to 10 carbon atoms, more preferably 1, 2, 3, 4, 5, or 6 carbons. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "aryl", as used herein, refer to 5- or 6-membered aromatic rings or connected systems thereof. Representative examples of 5- to 6-membered aromatic rings rings include, but are not limited to, phenyl, cyclopentadienyl, naphthyl, anthracyl, and phenanthryl. Aryl groups of the invention can be substituted with hydrogen, alkyl, alkoxy, thioalkoxy, carboxy, carboxyalkyl, or halogen. Aryl groups can be substituted with as many or as few non-hydrogen substitutents as valence allows. Aryl groups of the invention may be present as tautomers.

The term "heteroaryl", as used herein, refers to an aryl group containing at least one heteroatom independently selected from nitrogen, oxygen, or sulfur; or a tautomer thereof. Such a system of rings can be monocyclic or polycyclic as further described herein. Examples of such rings include, but are not limited to, rings wherein one carbon is replaced with an O or atom; where one, two, or three N atoms are arranged in a suitable manner to provide aromaticity; or where two carbon atoms in the ring are replaced with one O or S atom and one N atom. Such rings can include, but are not limited to, a six-membered aromatic ring wherein one to four of the ring carbon atoms are replaced by nitrogen atoms, five-membered rings containing a sulfur, oxygen, or nitrogen in the ring; five membered rings containing one to four nitrogen atoms; and five membered rings containing an oxygen or sulfur and one to three nitrogen atoms. Representative examples of 5- to 6-membered heteroaryl rings include, but are not limited to, furyl, imidazolyl, isoxazolyl, isothiazolyl, oxazolyl, pyrazinyl, pyrazolyl, pyridazinyl, pyridinyl, pyrimidinyl, pyrrolyl, tetrazolyl, [1,2,3]thiadiazolyl, [1,2,3]oxadiazolyl, thiazolyl, thienyl, [1,2,3]triazinyl, [1,2,4]triazinyl, [1,3,5]triazinyl, [1,2,3]triazolyl, and [1,2,4]triazolyl. Bicylic systems include benzofuran, benzothiazole, indolyl and azaindolyl, among many others. Heteroaryl groups can be substituted with hydrogen, alkyl, alkoxy, thioalkoxy, carboxy, carboxyalkyl, or halogen. Heteroaryl groups can be substituted with as many or as few non-hydrogen substitutents as valence allows. In certain Formulas of the invention including heteroaryl groups, for ease of depiction aromaticity has been illustrated using alternating double bonds; in some hereroaryl groups, the most stable aromatic structure may be different and the Formulas are intended to encompass such structures also.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy. The terms "alkthiolyl" and "thioalkoxy" as used herein refer to the analogous group containing sulfur rather than oxygen. Representative examples of thioalkoxy include, but are not limited to, methylthio, ethylthio, and propylthio.

The term "carbonyl" as used herein means a —C(=O)— group.

The term "carboxy" as used herein means a —COOH group, which may be protected as an ester group: —COO-alkyl.

The term "fluoro" as used herein means —F.

The term "halo" or "halogen" as used herein means Cl, Br, I, or F. The term "halide" as used herein means their corresponding radicals.

The term "hydroxy" as used herein means an —OH group.

The term "sulfonyl" as used herein means a —SO$_2$— group.

Unless otherwise indicated, the term "protecting group" or "protective group," when used to refer to part of a molecule subjected to a chemical reaction, means a chemical moiety that is not reactive under the conditions of that chemical reaction, and which may be removed to provide a moiety that is reactive under those conditions. Protecting groups are well known in the art. See, e.g., Greene, T. W. and Wuts, P. G. M., Protective Groups in Organic Synthesis (3 rd ed., John Wiley & Sons: 1999); Larock, R. C., Comprehensive Organic Transformations (2 nd ed., John Wiley & Sons: 1999). Some examples include benzyl, diphenylmethyl, trityl, Cbz, Boc, Fmoc, methoxycarbonyl, ethoxycarbonyl, and pthalimido. Protecting groups include, for example, nitrogen protecting groups and hydroxy-protecting groups.

The term "pseudohalide" as used herein means electron-rich substituents that chemically mimic halides and that could act as a leaving group in the catalyzed cross-coupling reaction. Exemplary pseudohalide groups include: cyano, isocyano, thiocyano, azido, —O-tosyl ("—OTs"), —O—SO$_2$CF$_3$ ("—OTf"), —O—SO$_2$CH$_3$ ("—OMs"), and —OSO$_2$-1H-imidazole ("imidazolylSO$_3$").

The use of parentheses in general chemical expressions is intended to mean that the chemical name is considered to encompass compounds with and without the noted term. For example: (hetero)aryl is intended to encompass both aryl and heteroaryl; and (hetero)aryl (pseudo)halide is intended to encompass aryl halide, heteroaryl halide, aryl pseudohalide, and heteroaryl pseudohalide.

The term "each independently" means that a particular set of R groups, all of which share a set of possibilities, can each be arbitrarily assigned to have a different possibility or the same possibility, and that this independence of assignment extends to the type of functionality selected. For example, "$R_x$ and $R_y$ are each independently H or alkyl" means not only that both $R_x$ and $R_y$ can each be alkyl, but each can be different groups from the noted list. For example: $R_x$ and $R_y$ can both be methyl; or $R_x$ can be methyl and $R_y$ can be ethyl; or $R_x$ can be H and $R_y$ can be methyl.

The term "substantially pure" means that the isolated material is at least 90% pure, preferably 95% pure, even more preferably 99% pure as assayed by analytical techniques known in the art.

It should be noted that a chemical moiety that forms part of a larger compound may be described herein using a name commonly accorded it when it exists as a single molecule or a name commonly accorded its radical. For example, the terms "pyridine" and "pyridyl" are accorded the same meaning when used to describe a moiety attached to other chemical moieties. Thus, for example, the two phrases "XOH, wherein X is pyridyl" and "XOH, wherein X is pyridine" are accorded the same meaning, and encompass the compounds pyridin-2-ol, pyridin-3-ol and pyridin-4-ol. Isomers Certain compounds of the present invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Certain compounds of the present invention may exist as cis or trans isomers, wherein substituents on a ring may attach in such a manner that they are on the same side of the ring (cis) relative to each other, or on opposite sides of the ring relative to each other (trans). Such methods are well known to those of ordinary skill in the art, and may include separation of isomers by recrystallization or chromatography. It should be understood that the compounds of the invention may possess tautomeric forms, as well as geometric isomers, and that these also constitute an aspect of the invention.

Exemplary Nickel-Based Pre-Catalysts

Compounds of formulas (VIII) and (IX) were made using the synthetic strategy illustrated in FIG. 1. The compound of formula (VIII) corresponds to the compound identified as P1. The compound of formula (IX) corresponds to the compound identified as P2.

Briefly, the treatment of $^{Me}$CgPH with 2-bromoiodobenzene under palladium-catalyzed C—P cross-coupling conditions afforded the halogenated $^{Me}$CgPPh derivative 1 in 86% isolated yield. The racemic reagent $^{Me}$CgPH is an air-stable solid that may be prepared in multi-gram quantities by way of a high-yielding hydrophosphination-condensation cascade commencing from inexpensive acetylacetone and phosphine.

Subsequent lithiation of halogenated $^{Me}$CgPPh derivative 1, followed by quenching with P(o-Tol)$_2$PCl afforded the air-stable target ligand "PAd-DalPhos" (L1) in quantitative yield. The ligand "PAd-DalPhos" (L1) corresponds to the compound of Formula (V).

Treatment of a compound of Formula (V) with NiCl$_2$ (DME) provides a pre-catalyst termed "(PAd-DalPhos) NiCl$_2$" (identified as "P2" in FIG. 1). Treatment of (PAd-DalPhos)NiCl$_2$ (P2) with ortho-tolylmagnesium chloride provides a pre-catalyst termed "(PAd-DalPhos)Ni(o-tolyl) Cl" (identified as "P1" in FIG. 1).

Synthesis of 1,3,5,7-tetramethyl-2,4,6-trioxaphosphaadamanatane-phenylbromide, 1

To a glass screw-capped vial containing a magnetic stir bar was added 2-bromoiodobenzene (0.73 ml, 5.7 mmol, 1.05 equiv), toluene (9.0 ml), Pd(PPh$_3$)$_4$ (0.330 g, 0.285 mmol), K$_2$CO$_3$ (1.571 g, 11.4 mmol, 2.0 equiv) and 1,3,5, 7-tetramethyl-2,4,8-trioxaphosphaadamantane (1.14 g, 5.3 mmol). The vial was sealed with a poly(tetrafluoroethylene) (PTFE)-lined cap and was removed from the glovebox. The vial was placed in an oil bath set to 110° C. and magnetic stirring was initiated. After 48 h (unoptimized), the reaction mixture was cooled, diluted with CH$_2$Cl$_2$ (50 ml) and washed with distilled water (3×50 ml). The organic layer was dried over anhydrous Na$_2$SO$_4$, filtered and the collected eluent solution was concentrated under reduced pressure by use of a rotary evaporator. The resulting yellow oil was filtered through an alumina plug (ca 50 g) eluting with 90% hexanes/CH$_2$Cl$_2$; the solvent was then removed from the collected eluent under reduced pressure by use of a rotary evaporator. The resulting yellow solid was purified by flash chromatography over silica, eluting with 10% ethyl acetate/ hexanes to afford 1 as a white solid (1.69 g, 86% yield). $^1$H NMR: (CDCl$_3$, 500 MHz) 8.29 (d, J=7.7, 1H), 7.66-7.64 (m, 1H), 7.37 (apparent t, J=7.5 Hz, 1H), 7.25 (apparent t, J=7.6 Hz, 1H), 2.14 (m, 1H), 2.02-1.89 (m, 2H), 1.55-1.44 (m, 13H). $^{13}$C{$^1$H} NMR: (CDCl$_3$, 125.8 MHz) 135.3 (d, J=22.6 Hz), 135.2, 133.8 (d, J=2.5 Hz), 133.2 (d, J=37.7 Hz), 131.0, 127.5, 97.0, 96.2, 74.5 (d, J=10.1 Hz), 73.9 (d, J=25.2 Hz), 45.8 (d, J=20.1 Hz), 36.5, 28.7 (d, J=18.9 Hz), 28.2, 27.9, 26.7 (d, J=11.3 Hz). $^{31}$P{$^1$H} NMR: (CDCl$_3$, 202.5 MHz) −29.6. High resolution mass spectrometry-electrospray ionization (HRMS-ESI) (m/z): calculated for C$_{16}$H$_{20}$$^{79}$BrNaO$_3$P [M+Na]: 393.0226; found: 393.0214.

Synthesis of PAd-DalPhos, L1.

Compound 1 and diethyl ether (~0.3 M in 1) were added to a glass screw-capped vial containing a magnetic stir bar. The vial was sealed with a cap featuring a PTFE septum. The solution was then cooled to −33° C. and magnetic stirring was initiated, followed by dropwise addition of n-butyllithium (1.5 equiv, 2.5 M in hexanes) via syringe. The resulting mixture was left to stir for 30 min while warming to ambient temperature.

At this point, chlorodi-(o-tolyl)phosphine (3.5 g, 14.1 mmol, 1.2 eq.) was added dropwise via syringe with continued stirring. The resulting mixture was left to stir for 48 h (unoptimized) at ambient temperature, after which the crude reaction mixture was opened to air on the benchtop and was filtered through a short Celite plug; the collected eluent was concentrated by use of a rotary evaporator. The residue was adsorbed onto silica (ca 1 g) and was then concentrated to dryness by use of a rotary evaporator. The so-formed silica dry pack was added to a silica plug (ca 50 g), and 10% EtOAc/hexanes (ca 300 ml) was passed through the plug. The collected eluent was then concentrated to dryness by use of a rotary evaporator, was washed with cold pentane (3×1.5 ml) and was then dried in vacuo to afford L1 as a white to off-white solid.

Alternative Compounds, L2-L4.

Alternative compounds which may be used as ligands in a nickel-based catalyst or pre-catalyst include the compounds illustrated below where, in the context of Formula (I): A and A' are bonds; X and Y are C; R$_3$-R$_5$ are H; R$_6$-R$_9$ are methyl; and R$_1$ and R$_2$ are: phenyl ("L2"), iso-propyl ("L3"), or cyclohexyl ("L4").

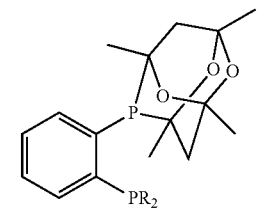

L1, R = o-tolyl, 80%
(PAd-DalPhos)
L2, R = Ph, 63%
L3, R = iPr, 68%
L4, R = Cy, 53%

Compounds L2-L4 may be made following the procedures outlined above with respect to L1, substituting the appropriate chlorophosphine (R$_2$ClP, R=Ph, iPr, Cy; 1.2 equiv) for the chlorodi-(o-tolyl)phosphine used to form compound L1.

NMR Data for L1-L4 and P1.

Note that the NMR spectral assignments for L1-L4 and P1 in some cases was rendered complex by: the C$_1$-symmetric nature of these species owing to the chiral (racemic) phosphaadamantane group; second-order coupling; dynamic behaviour (as evidenced in the temperature-dependent $^{31}P\{^{1}H\}$ NMR spectra of L1) and possibly in the case of P1 dynamic equilibria involving rotamers and/or between tetrahedral and square planar species.

Data for L1.

$^{1}$H NMR: (CDCl$_3$, 300 MHz) 8.32 (m, 1H), 7.39 (m, 1H), 7.29-7.21 (m, 5H), 7.11-7.04 (m, 2H), 6.89-6.87 (m, 1H), 6.79 (dd, J=7.2, 3.1 Hz, 1H), 6.64 (m, 1H), 2.42 (s, 3H), 2.36 (s, 3H), 2.14-1.79 (m, 3H), 1.57-1.21 (m, 13H). $^{13}$C$\{^{1}H\}$ NMR: (CDCl$_3$, 125.8 MHz) 142.7-142.2 (m), 134.2, 133.5, 130.3-130.0 (m), 128.8-128.6 (m), 126.4, 125.8, 97.2, 96.3, 74.5-74.2 (m), 46.1 (d, J=18.9 Hz), 36.6, 28.4-28.0 (m), 26.3 (d, J=11.3 Hz), 21.7, 21.5. $^{31}$P$\{^{1}H\}$ NMR: (CDCl$_3$, 202.5 MHz, 298K) −24.1 (broad m), −37.7 (d, J=166 Hz). $^{31}$P$\{^{1}H\}$R: (CDCl$_3$; 121.5 MHz, 223K) −23.8 (d, J=160 Hz, major species), −30.2 to −33.0 (broad m, minor species), −38.8 (d, J=177 Hz, minor species), −39.4 (d, J=160 Hz, major species). HRMS-ESI (m/z) Calcd for C$_{30}$H$_{34}$NaO$_3$P$_2$ [M+Na]: 527.1881; Found: 527.1875. Anal. Calcd for C$_{30}$H$_{34}$O$_3$P$_2$: C, 71.42; H, 6.79. Found: C, 71.12; H, 6.84.

Data for L2.

$^{1}$H NMR: (CDCl$_3$, 500 MHz) 8.36-8.33 (m, 1H), 7.40-7.30 (m, 10H), 7.23-7.19 (m, 2H), 7.02-6.99 (m, 1H), 2.12-2.07 (m, 2H), 1.94 (m, 1H), 1.56-1.53 (m, 1H), 1.49 (s, 3H), 1.43-1.40 (m, 6H), 1.33 (d, J=12.4 Hz, 3H). $^{13}$C$\{^{1}H\}$ NMR: (CDCl$_3$, 125.8 MHz) 147.5-147.1 (m), 140.5-140.0 (m), 137.9-137.5 (m), 134.6 (m), 134.2 (m), 133.5 (m), 129.9, 128.9-128.6 (m), 128.4 (two signals), 97.1, 96.2, 74.6, 74.5 (m), 46.1 (d, J=18.9 Hz), 36.6, 28.4-28.0 (m), 26.5 (d, J=11.3 Hz). $^{31}$P$\{^{1}H\}$ NMR: (CDCl$_3$, 202.5 MHz) −12.5 (d, J=168 Hz, 1P), −37.6 (d, J=168 Hz, 1P). HRMS-ESI (m/z) Calcd for C$_{30}$H$_{34}$NaO$_3$P$_2$ [M+Na]: 499.1562; Found: 499.1562.

Data for L3.

$^{1}$H NMR: (CDCl$_3$, 300 MHz) 8.36-8.31 (m, 1H), 7.59 (m, 1H), 7.40-7.36 (m, 2H), 2.42-2.36 (m, 1H), 2.20-1.87 (m, 4H), 1.46-1.36 (m, 13H), 1.24 (dd, J=15.4, 6.8 Hz, 3H), 1.14 (m, 3H), 1.01-0.90 (m, 6H). $^{13}$C$\{^{1}H\}$ NMR: (CDCl$_3$, 125.8 MHz) 134.1, 133.5 (m), 132.4 (m), 129.1 (two signals), 128.7 (m), 97.1, 96.2, 74.8. 74.7, 74.3-74.0 (m), 46.3 (d, J=20.1 Hz), 36.4, 28.4-28.0 (m), 26.7 (d, J=11.3 Hz), 22.9 (m), 20.7-19.8 (m), 18.0. $^{31}$P$\{^{1}H\}$ NMR: (CDCl$_3$, 202.5 MHz) −38.5 to −39.2 (m). HRMS-ESI (m/z) Calcd for C$_{30}$H$_{34}$ NaO$_3$P$_2$ [M+Na]: 431.1875; Found: 431.1867.

Data for L4.

$^{1}$H NMR: (CDCl$_3$, 500 MHz) 8.35-8.33 (m, 1H), 7.68 (broad s, 1H), 7.42-7.40 (m, 2H), 2.19-1.09 (m, 38H). $^{13}$C$\{^{1}H\}$ NMR: (CDCl$_3$, 125.8 MHz) 134.0, 133.1, 128.8, 128.5, 97.1, 96.2, 74.7 (two signals), 74.2 (m), 46.4 (d, J=18.9 Hz), 37.0-36.4 (m), 33.0-32.8 (m), 31.1-30.0 (m), 28.4-26.6 (m). $^{31}$P$\{^{1}H\}$ NMR: (CDCl$_3$, 202.5 MHz) −14.0 (broad m), −39.6 (broad m). HRMS-ESI (m/z) Calcd for C$_{28}$H$_{43}$O$_3$P$_2$ [M+H]: 489.2687; Found: 489.2682.

Some nickel-based catalysts or pre-catalysts made with ligand L1 may be more efficacious than corresponding nickel-based catalysts or pre-catalysts made with ligands L2-L4. Without wishing to be bound by theory, the authors of the present disclosure believe that increased steric bulk is particularly important in engendering useful catalytic behavior within the nickel-catalyzed C(sp$^2$)-N cross-coupling reactions of the present disclosure. Ligand L1 provides such increased steric bulk through the presences of the ortho-methyl group on the o-tolyl groups.

Synthesis of (PAd-DalPhos)NiCl$_2$, P2.

Figure 2A:
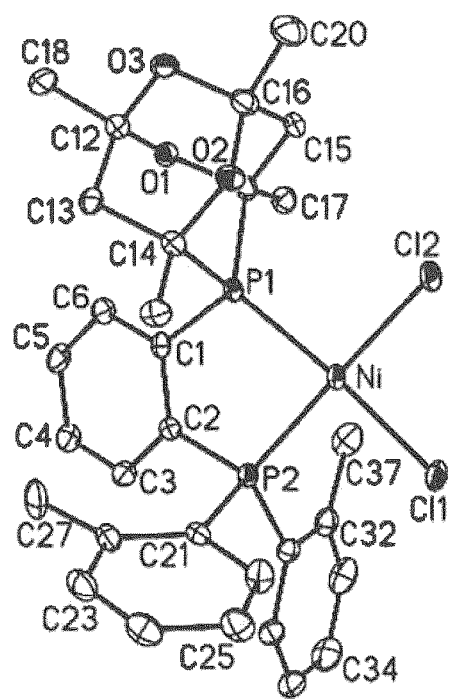
FIG. 2A is an illustration of the crystal structure of a nickel-based pre-catalyst according to the present disclosure. The pre-catalyst corresponds to the compound of Formula (IX), also referred to as "(PAd-DalPhos)NiCl$_2$" or "P2".

In a dinitrogen filled glovebox, a 100-ml oven-dried round bottom flask containing a magnetic stir bar was charged with NiCl$_2$(DME) (1.78 g, 8.10 mmol) and L1 (PAd-DalPhos; 4.54 g, 9.00 mmol, 1.1 equiv). The solid mixture was dissolved in ca 90 ml of tetrahydrofuran (THF) and the resulting solution was stirred magnetically at room temperature for 1 h. The crude reaction mixture was poured directly onto a glass frit and was washed with pentane (5×30 ml). The remaining solid on the frit was dissolved by passing CH$_2$Cl$_2$ through the frit (ca 50 ml), followed by collection of the eluent. The solvent was removed in vacuo affording the desired product (P2) as a dark purple paramagnetic solid (3.93 g, 77%). Anal. calculated for C$_{30}$H$_{34}$Cl$_2$NiO$_3$P$_2$ C, 56.82; H, 5.40. Found: C, 56.72; H, 5.65. A single crystal suitable for X-ray diffraction analysis was prepared by slow evaporation of pentane into a solution of CH$_2$Cl$_2$ at room temperature. The crystal structure of P2 is depicted in FIG. 2A.

Synthesis of (PAd-DalPhos)Ni(o-tolyl)Cl, P1.

Figure 2B:
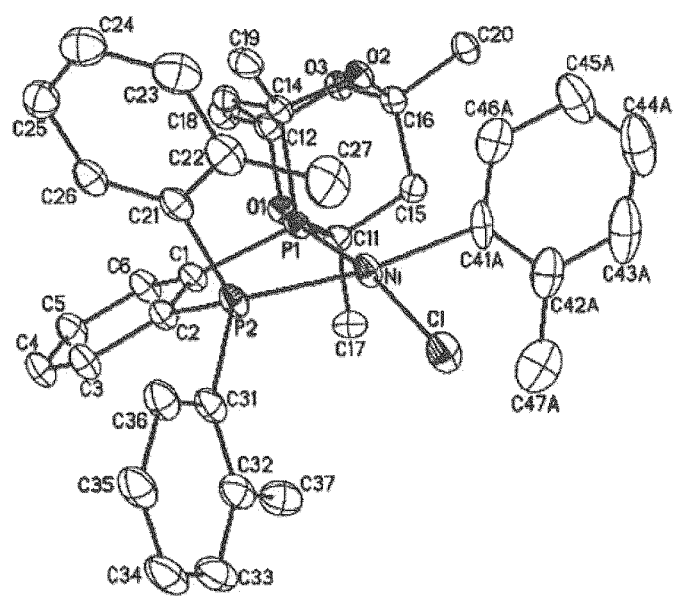
FIG. 2B is an illustration of the crystal structure of another nickel-based pre-catalyst according to the present disclosure. The pre-catalyst corresponds to the compound of Formula (VIII), also referred to as "(PAd-DalPhos)Ni(o-tolyl)Cl" or "P1".

(PAd-DalPhos)NiCl$_2$ (3.90 g, 6.15 mmol) and THF (62 ml) were added to an oven-dried 100 ml round-bottom flask containing a magnetic stir bar. Magnetic stirring was initiated and ortho-tolylmagnesium chloride was then added dropwise (7.40 ml, 7.40 mmol, 1.2 equiv, 1.0 M in THF) to the heterogeneous mixture, resulting in an immediate colour change from red to orange. The reaction mixture was allowed to stir at room temperature for 2 h. The reaction mixture was subsequently treated with MeOH (5 ml) in air, and then was reduced to dryness in vacuo. The residue was treated with cold MeOH (0° C., 15 ml), and the crude reaction mixture was then filtered through a glass frit, affording a retained orange solid that was washed with additional cold MeOH (0° C., 3×10 ml), followed by pentane (3×50 ml). The orange solid on the frit was then dissolved via addition of CH$_2$Cl$_2$ (50 ml). Collection of the eluent followed by removal solvent afforded (PAd-DalPhos) Ni(o-tolyl)Cl (P1), as an orange solid (3.95 g, 93% yield). The existence of a major and minor disastereomers (ca 2:1) in solution is suggested on the basis of $^{31}$P$\{^{1}H\}$ NMR data. $^{1}$H NMR (CDCl$_3$, 500 MHz): 8.74 (m, 1H), 7.59-7.09 (m, 10H), 6.86-6.67 (m, 5H), 3.33-2.59 (m, 9H), 1.98-1.93 (m, 1H), 1.59-1.53 (m, 6H), 1.42 (s, 3H), 1.10-0.92 (s, 6H). $^{13}$C$\{^{1}H\}$ NMR (CDCl$_3$, 125.8 MHz): 145.9 (m), 145.8 (m), 143.4-143.2 (m), 136.7-133.1 (m), 132.0-130.9 (m), 129.6-128.6 (m), 126.3-125.8 (m), 124.7 (m), 123.8 (m), 122.7, 97.8-96.2 (m), 40.2-39.6 (m), 28.8-24.2 (m). $^{31}$P$\{^{1}H\}$ NMR (CDCl$_3$, 202.5 MHz): 32.6 (d, J=4.3 Hz, minor species), 31.5 (d, J=4.6 Hz, major species), 27.6 (d, J=4.6 Hz, major species), 26.5 (d, J=4.3 Hz, minor species). On the basis of the observed positional disorder associated with the Ni-bound ortho-tolyl fragment within the X-ray structure of P1, arising from Ni—C(tolyl) bond rotation (80:20 occupancy ratio), we interpret the major and minor species as being rotamers of this type. Anal. calculated for C$_{37}$H$_{41}$ClNiO$_3$P$_2$ C, 64.42; H, 5.99. Found: C, 64.11; H, 5.84. A single crystal suitable for X-ray diffraction analysis was prepared by slow evaporation of pentane into a solution of CH$_2$Cl$_2$ at room temperature. The crystal structure of P1 is depicted in FIG. 2B.

Additional Exemplary Nickel-Based Pre-Catalysts

Figure 3A:
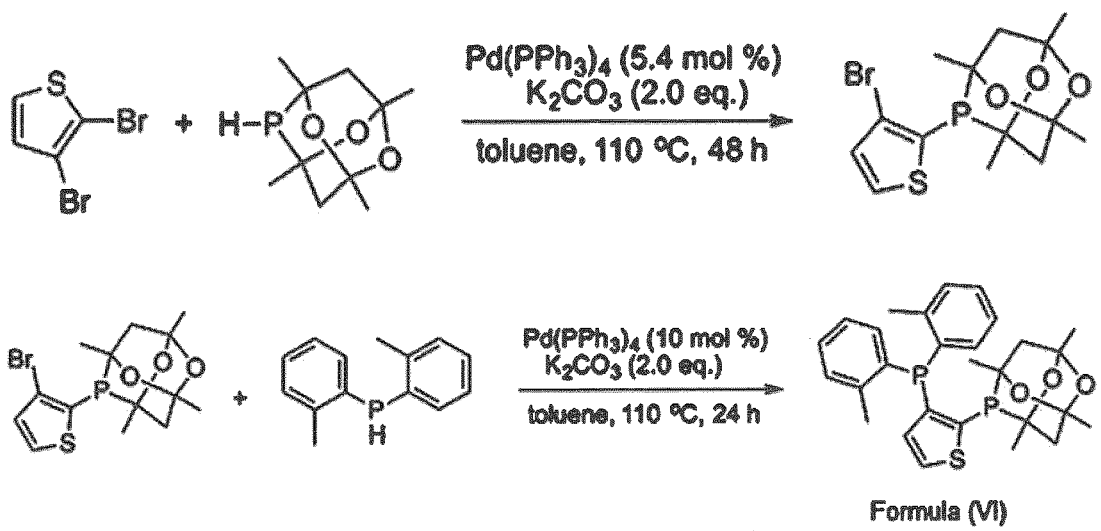
FIG. 3A is an illustration of a synthetic scheme which may be used to produce a ligand for a catalyst or pre-catalyst according to the present disclosure.
Figure 3B:
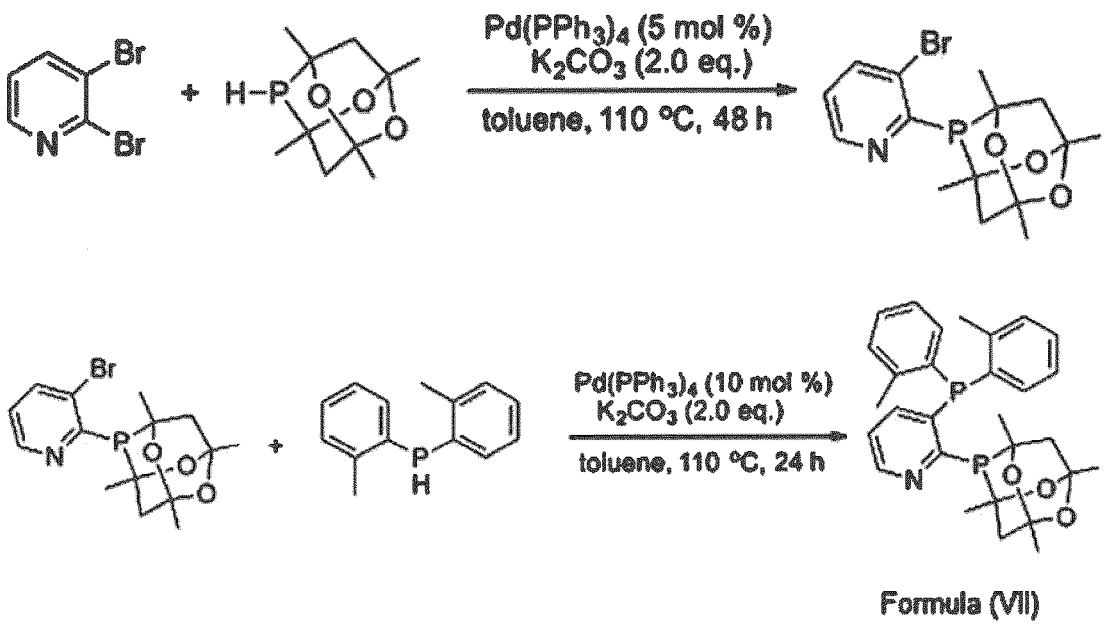
FIG. 3B is an illustration of a synthetic scheme which may be used to produce a ligand for a catalyst or pre-catalyst according to the present disclosure.

Compounds of Formulas (VI) and (VII) were made using the synthetic strategy illustrated in FIGS. 3A and 3B, respectively.

Synthesis of a Compound of Formula (VI).

In a dinitrogen filled glovebox 2,3-dibromothiophene (0.17 mL, 1.5 mmol, 1.05 eq) was added to a toluene (10.0 mL) solution of Pd(PPh$_3$)$_4$ (0.094 g, 0.081 mmol, 0.054 eq), K$_2$CO$_3$ (0.395 g, 2.86 mmol, 2.0 eq), and 1,3,5,7-tetramethyl-2,4,8-trioxaphosphaadamantane (0.309 g, 1.43 mmol, 1.0 eq) in a 4-dram vial equipped with a stirbar. The vial was sealed with a screw cap containing a PTFE septum and was wrapped with Teflon tape. The vial was removed from the glovebox and placed in a temperature-controlled aluminum heating block set to 110° C., and was allowed to react under the influence of magnetic stirring for 48 hours. The solution was cooled to ambient temperature, diluted with 20 mL DCM and washed with distilled water (3×20 mL). The aqueous layer was subsequently washed with DCM (3×20 mL) and the organic layers were combined and dried over anhydrous $Na_2SO_4$, and the solvent was concentrated under reduced pressure. The resulting orange oil was filtered through a silica plug (ca. 25 g) eluting with 50% hexanes/ethyl acetate. The reaction mixture was adsorbed onto $SiO_2$ and then pumped down via rotary evaporation. The $SiO_2$ dry pack was purified by flash chromatography over $SiO_2$ eluting with 5% ethyl acetate/hexanes to afford 8-(3-bromothiophen-2-yl)-1,3,5,7-tetramethyl-2,4,6-trioxa-8-phosphaadamanatane) as a white solid (0.27 g, 50% yield). $^1$H NMR: (CDCl$_3$, 500 MHz) 7.58-7.57 (dd, J=5.2, 1.4 Hz, 1H), 7.10-7.09 (dd, J=5.1, 2.5 Hz, 1H), 2.08-2.04 (m, 2H), 2.00-1.93 (m, 1H), 1.55-1.51 (m, 2H), 1.47-1.42 (m, 8H), 1.38-1.35 (m, 3H). $^{31}$P{$^1$H} NMR: (CDCl$_3$, 202.5 MHz) −37.6 (s, 1P). $^{13}$C{$^1$H} NMR: (CDCl$_3$, 125.8 MHz) 133.3, 131.2, 97.0, 96.5, 74.2, 73.0, 45.0, 44.8, 37.1, 28.3, 28.1, 28.0, 27.9, 27.4, 27.3.

In a dinitrogen filled glovebox a 4-dram vial equipped with a stirbar was charged with 8-(3-bromothiophen-2-yl)-1,3,5,7-tetramethyl-2,4,6-trioxa-8-phosphaadamanatane) (0.055 g, 0.227 mmol, 1.0 eq), Pd(PPh$_3$)$_4$ (0.026 g, 0.023 mmol, 0.1 eq), K$_2$CO$_3$ (0.063 g, 0.454 mmol, 2.0 eq), di(o-tolyl)phosphine (0.049 g, 0.227 mmol, 1.0 eq) in a 4-dram vial equipped with a stirbar, and toluene (1.5 mL). The vial was sealed with a screw cap containing a PTFE septum and was wrapped with Teflon tape. The vial was removed from the glovebox and placed in a temperature-controlled aluminum heating block set to 110° C., and was allowed to react under the influence of magnetic stirring for 24 hours. The solution was cooled to ambient temperature, diluted with ethyl acetate (20 mL) and filtered through a Celite plug (ca. 10 g). The reaction mixture was adsorbed onto $SiO_2$ and then pumped down via rotary evaporation. The $SiO_2$ dry pack was purified by flash chromatography over $SiO_2$ eluting with 5% ethyl acetate/hexanes to afford a light purple solid. The solid was washed with room-temperature pentane (2×5 mL) to afford compound of formula (VI) as an off-white solid (0.05 g, 41% yield). $^1$H NMR: (CDCl$_3$, 300 MHz) 7.58 (d, J=5.0, 1H), 7.24-7.20 (m, 3H), 7.17-7.15 (m, 1H), 7.09-7.03 (m, 2H), 6.82-6.79 (m, 1H), 6.71-6.68 (m, 1H), 6.59-6.58 (m, 1H), 2.41 (s, 3H), 2.32-2.29 (m, 4H), 2.09-2.04 (m, 1H), 2.00-1.89 (m, 1H), 1.57-1.53 (m, 1H), 1.47 (s, 3H), 1.38 (s, 3H), 1.34-1.31 (m, 3H), 1.08-1.05 (m, 3H). $^{31}$P{$^1$H} NMR: (CDCl$_3$, 202.5 MHz, 298K) −38.5 (d, J$_{P,P}$=135.7 Hz, 1P), −42.0 (d, J$_{P,P}$=133.7 Hz, 1P). $^{13}$C{$^1$H} NMR: (CDCl$_3$, 125.8 MHz) 149.6, 149.5, 149.4, 149.3, 142.7, 142.5, 142.1, 141.9, 136.7, 135.9, 135.8, 133.4, 132.9, 132.1, 130.3, 128.9, 128.7, 126.3, 126.0, 97.1, 96.5, 73.9, 73.8, 73.5, 73.4, 73.3, 45.1, 45.0, 37.5, 28.2, 27.9, 27.8, 27.0, 21.6, 21.4, 21.3.

Synthesis of a Compound of Formula (VII).

In a dinitrogen filled glovebox a 4-dram vial equipped with a stirbar was charged with 2,3-dibromopyridine (0.133 g, 0.564 mmol, 1.05 eq), Pd(PPh3)4 (0.031 g, 0.0269 mmol, 0.05 eq), K2CO3 (0.147 g, 1.07 mmol, 2.0 eq), 1,3,5,7-tetramethyl-2,4,8-trioxaphosphaadamantane (0.116 g, 0.537 mmol, 1.0 eq) and toluene (1.8 mL). The vial was sealed with a screw cap containing a PTFE septum and was wrapped with Teflon tape. The vial was removed from the glovebox and placed in a temperature-controlled aluminum heating block set to 110° C., and was allowed to react under the influence of magnetic stirring for 48 hours. The solution was cooled to ambient temperature, diluted with 20 mL DCM and washed with distilled water (3×20 mL The aqueous layer was subsequently washed with DCM (3×20 mL) and the organic layers were combined and dried over anhydrous Na2SO4, and the solvent was concentrated under reduced pressure. The resulting orange oil was purified by flash chromatography over SiO2 eluting with 10% ethyl acetate/hexanes to afford 3-bromo-2-(1,3,5,7-tetramethyl-2,4,6-trioxaphosphaadamanatan-8-yl)pyridine as a white solid (0.133 g, 67% yield). 1H NMR: (CDCl3, 500 MHz) 8.73-8.71 (m, 1H), 7.89-7.86 (m, 1H), 7.14-7.11 (m, 1H), 2.83 (d, J=13 Hz, 1H), 2.21-2.17 (dd, J=13.1, 7.3 Hz, 1H), 2.01-1.93 (dd, J=27.2 13.1, Hz, 1H), 1.61-1.58 (dd, J=13.1, 4.7 Hz, 1H), 1.53-1.44 (m, 12H). 31P{1H} NMR: (CDCl3, 202.5 MHz) −26.00 (s, 1P). 13C{1H} NMR: (CDCl3, 125.8 MHz) 159.2, 158.9, 148.5, 140.1, 140.0, 131.4, 131.1, 124.2, 97.2, 96.4, 74.9, 74.8, 74.6, 74.4, 46.0, 45.9, 37.2, 28.9, 28.7, 282., 28.0, 27.5, 27.4.

In a dinitrogen filled glovebox a 4-dram vial equipped with a stirbar was charged with 3-bromo-2-(1,3,5,7-tetramethyl-2,4,6-trioxaphosphaadamanatan-8-yl)pyridine (0.100 g, 0.269 mmol, 1.00 eq), Pd(PPh$_3$)$_4$ (0.031 g, 0.0269 mmol, 0.1 eq), K$_2$CO$_3$ (0.074 g, 0.538 mmol, 2.0 eq), and 1,3,5,7-tetramethyl-2,4,8-trioxaphosphaadamantane (0.116 g, 0.537 mmol, 1.0 eq) and toluene (3.0 mL). The vial was sealed with a screw cap containing a PTFE septum and was wrapped with Teflon tape. The vial was removed from the glovebox and placed in a temperature-controlled aluminum heating block set to 110° C., and was allowed to react under the influence of magnetic stirring for 24 hours. The solution was cooled to ambient temperature and was then filtered through a silica plug (ca. 25 g) eluting with 50% hexanes/ethyl acetate. The reaction mixture was adsorbed onto $SiO_2$ and the solvent was removed via rotary evaporation. The $SiO_2$ dry pack was purified by flash chromatography over $SiO_2$ eluting with 10% ethyl acetate/hexanes to yield a light pink solid. The crude product was washed with room-temperature pentane (3×5 mL) to afford compound of formula (IX) as a beige solid (0.089 g, 66% yield). $^1$H NMR: (CDCl$_3$, 300 MHz) 8.73-8.72 (m, 1H), 7.30-7.22 (m, 4H), 7.13-7.04 (m, 4H), 6.73-6.67 (m, 2H), 3.21 (d, J=12.5 Hz, 1H), 2.41-2.39 (m, 6H), 2.11-2.04 (dd, J=12.9, 7.1 Hz, 1H), 1.94-1.81 (dd, J=26.2, 12.9 Hz, 1H), 1.59-1.53 (dd, J=12.9, 5.0 Hz, 1H), 1.48 (s, 3H), 1.39 (s, 3H), 1.29-1.19 (m, 6H). $^{31}$P{$^1$H} NMR: (CDCl$_3$, 121.5 MHz) −29.50 (d, J$_{P,P}$=157.3 Hz, 1P), −34.40 (d, J$_{P,P}$=157.5 Hz, 1P). $^{13}$C{$^1$H} NMR: (CDCl$_3$, 75.5 MHz) 149.6, 142.6, 142.5, 142.3, 142.1, 140.3, 140.2, 134.7, 133.7, 130.2, 128.9, 128.8, 126.1, 123.3, 97.1, 96.4, 74.4, 73.9, 73.7, 45.8, 45.6, 36.9, 28.0, 27.9, 27.8, 26.6, 26.5, 21.4, 21.1.

Summary of Exemplary Methods Used to Test Cross-Coupling Reactions

Exemplary General Protocol Used to Couple Aryl Halides with Ammonia (GPA).

Unless otherwise specified, PAdDalPhosNi(o-tol)Cl (P1) (8.3-20.7 mg, 0.012-0.030 mmol, 2-5 mol %), aryl halide or aryl pseudohalide (0.60 mmol, 1 eq), and sodium tert-butoxide (115.3 mg, 1.20 mmol, 2.0 eq) were added to a screw capped vial containing a magnetic stir bar, followed by the addition of toluene (9 mL) and NH$_3$ as a 0.5M solution in 1,4-dioxane (1.8-4.2 mmol, 3-7 eq., 3.0-8.4 mL). The vial was sealed with a cap containing a PTFE septum, removed from the glovebox, placed in a temperature-controlled aluminum heating block set at 110° C. for 16 h. The vial was removed from the heating block and left to cool to ambient temperature.

Exemplary Workup Methods.

Purification by Extraction: The volatile materials were evaporated in vacuo. The residue was dissolved in EtOAc. The product was extracted with aqueous 1 M HCl (3×25 mL). The combined aqueous layers were then washed with EtOAc (3×10 mL). Solid sodium bicarbonate was added to the acidic aqueous layer until it was fully neutralized (monitored with pH paper). The product was extracted with EtOAc (3×25 mL). The organic fractions were combined, dried over $Na_2SO_4$, and filtered through a silica plug with ethyl acetate (~30 mL). The residual solvent was removed in vacuo and the product was allowed to dry overnight.

Purification by Chromatography.

The crude reaction mixture was filtered through a short Celite plug, and the volatile materials were evaporated in vacuo. The crude product was purified by flash-column chromatography to afford the purified product.

Exemplary General Protocol Used to Couple Heteroaryl Halides with Ammonia (GPB).

Unless specified otherwise, PAdDalPhosNi(o-tol)Cl (P1) (0.015 mmol, 3 mol %), aryl halide or aryl pseudohalide (0.5 mmol, 1 equiv) and lithium tert-butoxide (60.0 mg, 0.75 mmol, 1.5 eq) were added to a screw capped vial containing a magnetic stir bar, followed by the addition of toluene (4.2 ml) and $NH_3$ as a 0.5M solution in 1,4-dioxane (3.5 mmol, 7 equiv.). The vial was sealed with a cap containing a PTFE septum, removed from the glovebox, placed in a temperature-controlled aluminum heating block set at 110° C. for 16 h. The vial was removed from the heating block and left to cool to ambient temperature. The crude reaction mixture was dissolved in ethyl acetate (10 mL) and poured onto brine (10 mL). The layers were separated and the aqueous layer was extracted with ethyl acetate (2×10 mL). The organic fractions were combined, dried over $Na_2SO_4$ and concentrated under reduced pressure. The crude residue was purified by use of column chromatography or preparatory TLC over alumina or silica.

Exemplary General Protocol Used to Couple Aryl Halides with Primary Amines (GPC).

Unless specified otherwise, PAdDalPhosNi(o-tol)Cl (P1) (4.14 mg, 0.006 mmol), $K_3PO_4$ (152.8 mg, 0.72 mmol, 6.0 equiv), aryl mesylate (0.12 mmol, 1.0 equiv), followed by $NH_3$ as a 0.5 M solution in 1,4-dioxane (0.75 mmol, 6.25 equiv) were added to a screw-capped vial containing a magnetic stir bar. The vial was sealed with a cap containing a PTFE septum, removed from the glovebox, placed in a temperature-controlled aluminum heating block set at 110° C. for 16 hours. The vial was then removed from the heating block and was left to cool to ambient temperature. The crude reaction mixture was dissolved in ethyl acetate (10 mL) and poured onto brine (10 mL). The layers were separated and the aqueous layer was extracted with ethyl acetate (2×10 mL). The organic fractions were combined, dried over $Na_2SO_4$ and concentrated under reduced pressure. The crude residue was purified by use of column chromatography over alumina or silica.

Exemplary General Protocol for Microwave Reactions with Ammonium Salts (GPD).

PAdDalPhosNi(o-tol)Cl (P1) (6.9-34.5 mg, 0.01-0.05 mmol, 1-5 mol %), ammonium salt (5 equiv, 5 mmol), NaOtBu (6.5 equiv, 6.5 mmol) and aryl halide or aryl pseudohalide (1 mmol) were weighed into an oven-dried 20 mL microwave vial to which a magnetic stir bar had been added. Cyclopentyl methyl ether (CPME) (10 mL) was then added to the vial, the vial was sealed with an aluminum crimp cap featuring a PTFE/silicone septum, and was removed from the glovebox. The vial was then heated to the specified temperature in a Biotage Initiator+ microwave reactor for the specified time, using fixed-hold time. The vial was then removed from the microwave reactor and was left to cool to ambient temperature, at which point the reaction mixture was taken up in $CH_2Cl_2$ (ca. 50 mL) and was washed with distilled water (3×50 mL). The organic layer was dried over $Na_2SO_4$ and concentrated under reduced pressure. The crude residue was purified by use of column chromatography using a Biotage Isolera One automated column using a EtOAc:hexanes gradient on a 25 g Biotage Snap cartridge. Notably, while $NH_4OAc$ proved effective as an ammonia source in these reactions; the use of $NH_4Cl$, $(NH_4)_2SO_4$, $LiNH_2$ or $LiN(TMS)_2$ afforded negligible conversion to product on the basis of gas chromatographic analysis.

Exemplary General Protocol for Reactions Using Ammonia Gas (GPE).

Unless specified otherwise, a vial (1 dram, 3.696 mL) containing a magnetic stirbar was charged with PAdDalPhosNi(o-tol)Cl (P1) (0.018 mmol, 5 mol %), LiOtBu (43.2 mg, 0.54 mmol, 1.5 equiv), toluene (1.0 mL), and aryl halide or aryl pseudohalide (0.36 mmol, 1.0 equiv). The resulting solution was stirred briefly and then was sealed with a cap containing a PTFE septum; the septum was then punctured with a 26G1/2 PrecisionGlide needle and the needle was not removed until the final workup. The reaction vial was placed in a high-pressure reaction chamber purchased from the Parr Instrument Company (type 316 stainless steel, equipped with a thermocouple immersed in oil to allow for accurate external temperature monitoring within the reaction chamber proximal to the placement of the reaction vial), and the reaction chamber was sealed under nitrogen within the glovebox. The reaction chamber was removed from the glovebox, and was placed in an oil bath at room temperature that was mounted on top of a hot-plate/magnetic stirrer. The reaction chamber was fitted with a braided and PTFE-lined stainless steel hose designed for use with corrosive gases that was connected to a tank of anhydrous ammonia gas. Magnetic stirring was initiated and the reaction chamber was purged with ammonia for approximately five minutes, after which time the reaction chamber was pressurized with ammonia (114 psi maintained for 30 minutes at room temperature). The reaction chamber was then sealed, disconnected from the ammonia tank, and was heated at 110° C. for 16 h; pressure was built up to 150 psi over the course of the reaction. The reaction chamber was allowed to cool to room temperature, after which the contents of the reaction chamber were vented slowly within a fumehood. The products were removed from the pressure reaction chamber, the crude reaction mixture was dissolved in ethyl acetate (10 mL) and poured onto brine (10 mL). The layers were separated and the aqueous layer was extracted with ethyl acetate (2×10 mL). The organic fractions were combined, dried over $Na_2SO_4$ and concentrated under reduced pressure. The crude residue was purified by use of column chromatography or over silica.

Exemplary General Protocol for the Amination of Aryl Halides with Primary Amines (GPF).

Unless specified otherwise, PAdDalPhosNi(o-tol)Cl (P1) (10.3 mg, 0.015 mmol, 3 mol %), NaOtBu (72.3 mg, 0.75 mmol, 1.5 equiv), aryl halide or aryl pseudohalide (0.5 mmol, 1.0 equiv), amine (0.55 mmol, 1.1 equiv) and toluene (4.7 mL) were added to a screw-capped vial containing a magnetic stir bar. The vial was sealed with a cap containing a PTFE septum, was removed from the glovebox and placed in a temperature-controlled aluminum heating block set at the specified temperature, and was allowed to react under the influence of magnetic stirring for 16 h (unoptimized). The crude reaction mixture subsequently was dissolved in ethyl acetate (10 mL) and poured onto brine (10 mL). The layers were separated and the aqueous layer was extracted with ethyl acetate (2×10 mL). The organic fractions were combined, dried over $Na_2SO_4$ and concentrated under reduced pressure. The crude residue was purified by use of column chromatography over alumina or silica.

Exemplary General Protocol for the Amination of Aryl Halides with Methyl and Dimethylamine (GPG).

Unless specified otherwise, PAdDalPhosNi(o-tol)Cl (P1) (17.2 mg, 0.025 mmol, 5 mol %), NaOtBu (72.3 mg, 0.75 mmol, 1.5 equiv), and aryl halide or aryl pseudohalide (0.5 mmol, 1.0 equiv), followed by the addition of amine (2 M solution in THF, 1.75 mL, 3.5 mmol, 7.0 equiv) were added to a screw-capped vial containing a magnetic stir bar. The vial was sealed with a cap containing a PTFE septum, was removed from the glovebox and placed in a temperature-controlled aluminum heating block set at the specified temperature, and was allowed to react under the influence of magnetic stirring for 16 h (unoptimized). The crude reaction mixture subsequently was dissolved in ethyl acetate (10 mL) and poured onto brine (10 mL). The layers were separated and the aqueous layer was extracted with ethyl acetate (2×10 mL). The organic fractions were combined, dried over $Na_2SO_4$ and concentrated under reduced pressure. The crude residue was purified by use of column chromatography over alumina or silica.

Exemplary General Protocol for the Amination of Aryl Mesylates with Primary Amines (GPH).

Unless specified otherwise, PAdDalPhosNi(o-tol)Cl (P1) (17.2 mg, 0.025 mmol 5 mol %), $K_3PO_4$ (636.8 mg, 3 mmol, 6.0 equiv), aryl mesylate (0.5 mmol, 1.0 equiv), amine (0.55 mmol, 1.1 equiv) and CPME (2.0 mL) were added to a screw-capped vial containing a magnetic stir bar. The vial was sealed with a cap containing a PTFE septum, was removed from the glovebox and placed in a temperature-controlled aluminum heating block set at 110° C., and was allowed to react under the influence of magnetic stirring for 16 h (unoptimized). The crude reaction mixture subsequently was dissolved in ethyl acetate (10 mL) and poured onto brine (10 mL). The layers were separated and the aqueous layer was extracted with ethyl acetate (2×10 mL). The organic fractions were combined, dried over $Na_2SO_4$ and concentrated under reduced pressure. The crude residue was purified by use of column chromatography over alumina or silica.

Exemplary General Protocol for the Amination of Aryl Halides with Carbazole and Indoles (GPI).

Unless specified otherwise, PAdDalPhosNi(o-tol)Cl (P1) (13.8 mg, 0.02 mmol, 10 mol %), NaOtBu (57.6 mg, 0.60 mmol, 3.0 equiv), aryl halide (0.2 mmol, 1.0 equiv), amine (0.2 mmol, 1.0 equiv) and 1,4-dioxane (2.0 mL) were added to a screw-capped vial containing a magnetic stir bar. The vial was sealed with a cap containing a PTFE septum, was removed from the glovebox and placed in a temperature-controlled aluminum heating block set at 110° C., and was allowed to react under the influence of magnetic stirring for 16 h (unoptimized). The crude reaction mixture was dissolved in ethyl acetate (10 mL) and poured onto brine (10 mL). The layers were separated and the aqueous layer was extracted with ethyl acetate (2×10 mL). The organic fractions were combined, dried over $Na_2SO_4$ and concentrated under reduced pressure. The crude residue was purified by use of preparatory silica TLC.

Exemplary General Protocol Used to Couple Aryl Halides with Ammonia (GPJ).

Unless otherwise specified, the compound of Formula (VI) or (VII) (5 mol %), $Ni(COD)_2$ (5 mol %), aryl halide or aryl pseudohalide (1 eq), and sodium tert-butoxide (3 eq) were added to a screw capped vial containing a magnetic stir bar, followed by the addition of toluene (9 mL) and $NH_3$ as a 0.5M solution in 1,4 dioxane (3-7 eq). The reaction generates compounds of Formula (X) and (XI) in situ. The vial was sealed with a cap containing a PTFE septum, removed from the glovebox, and placed in a temperature-controlled aluminum heating block set at 110° C. for 16 h. The vial was removed from the heating block and left to cool to ambient temperature.

Exemplary Workup Methods.

Purification by Extraction: The volatile materials were evaporated in vacuo. The residue was dissolved in EtOAc. The product was extracted with aqueous 1 M HCl (3×25 mL). The combined aqueous layers were then washed with EtOAc (3×10 mL). Solid sodium bicarbonate was added to the acidic aqueous layer until it was fully neutralized (monitored with pH paper). The product was extracted with EtOAc (3×25 mL). The organic fractions were combined, dried over $Na_2SO_4$, and filtered through a silica plug with ethyl acetate (~30 mL). The residual solvent was removed in vacuo and the product was allowed to dry overnight.

Purification by Chromatography.

The crude reaction mixture was filtered through a short Celite plug, and the volatile materials were evaporated in vacuo. The crude product was purified by flash-column chromatography to afford the purified product.

Figure 5:
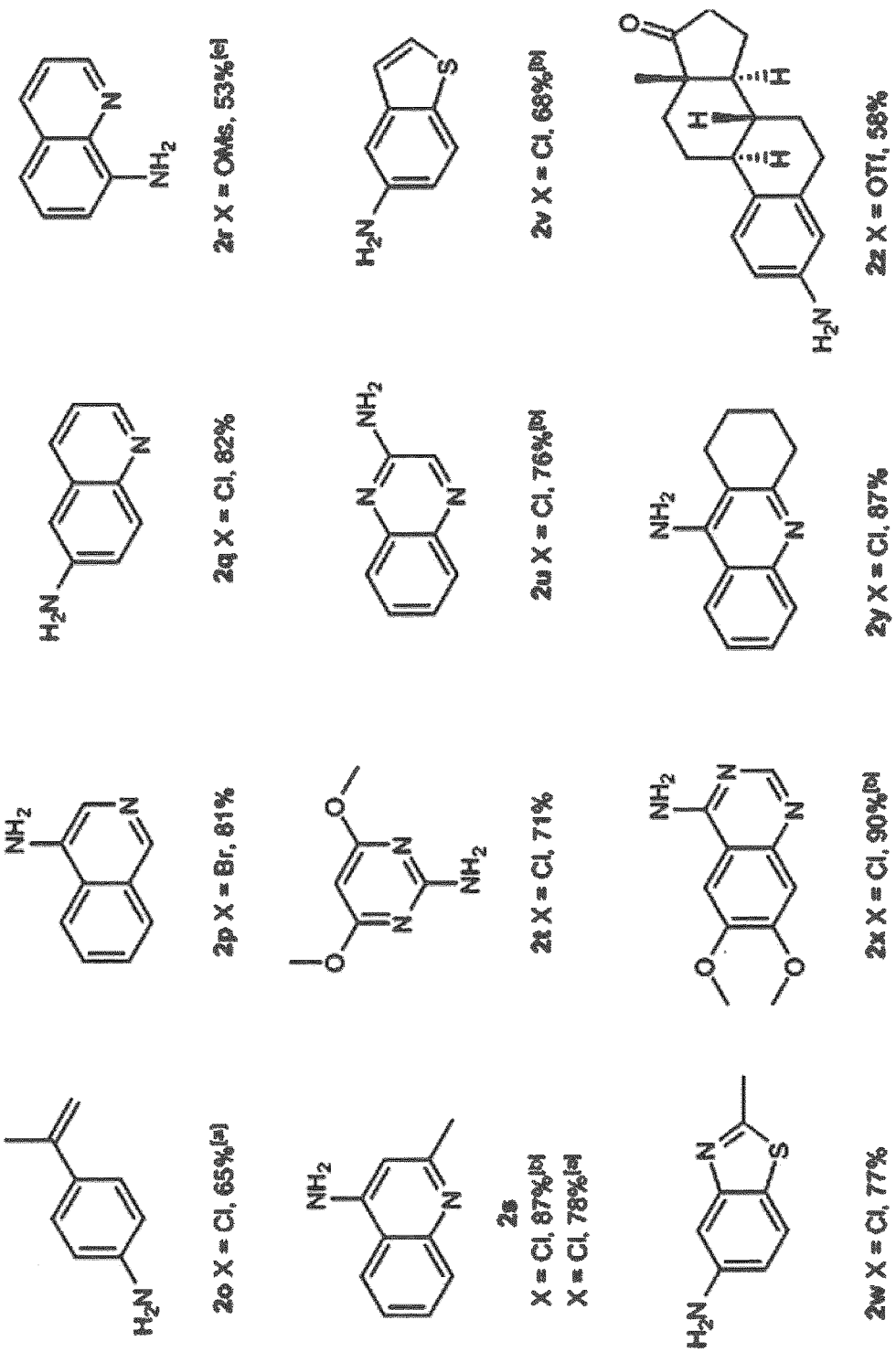
FIG. 5 is a list of exemplary chemical products synthesized using a variety of starting materials, and catalyzed using a pre-catalyst according to the present disclosure.
Figure 6:
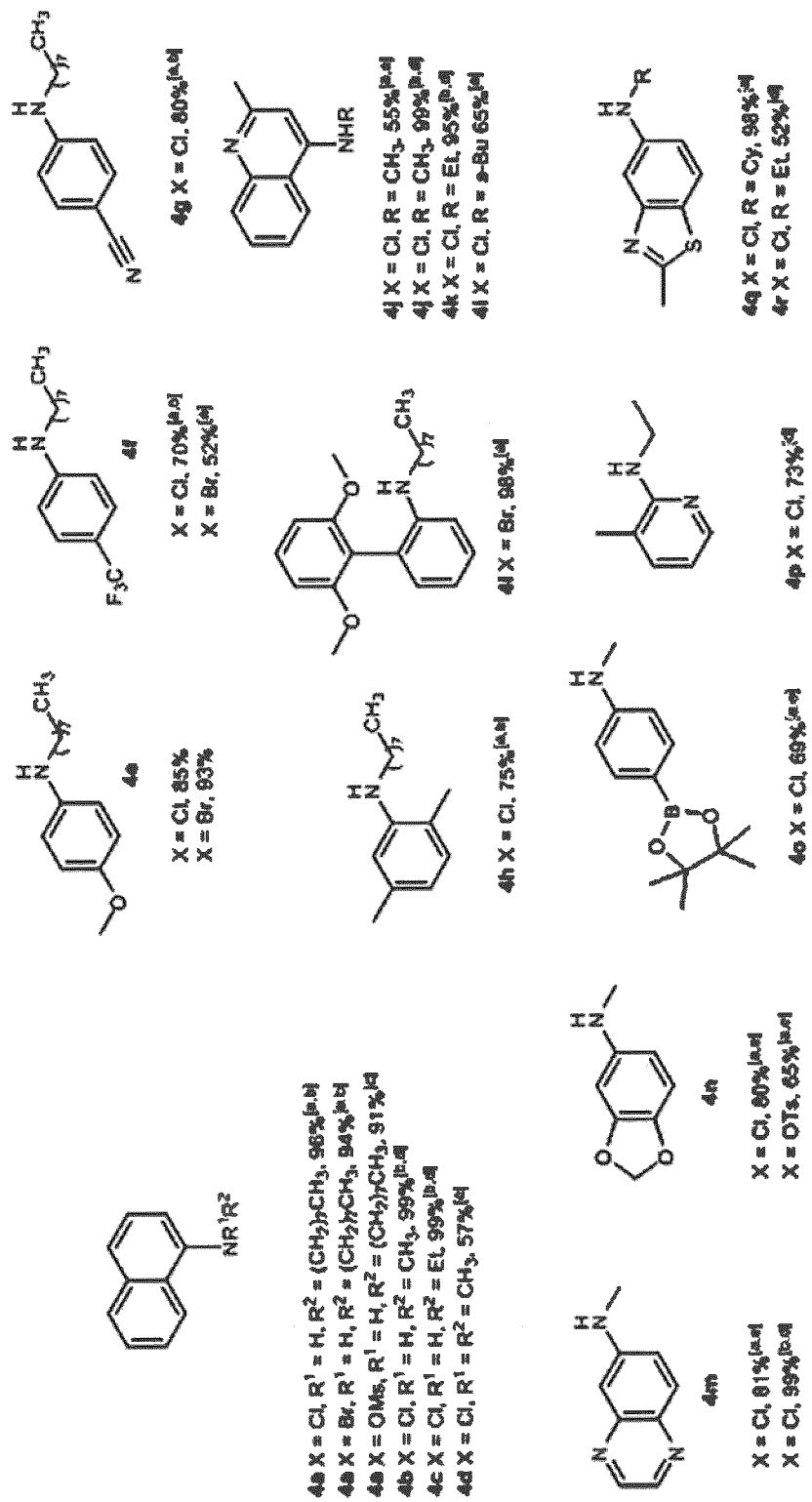
FIG. 6 is a list of exemplary chemical products synthesized using a variety of starting materials, and catalyzed using a pre-catalyst according to the present disclosure.
Figure 7:
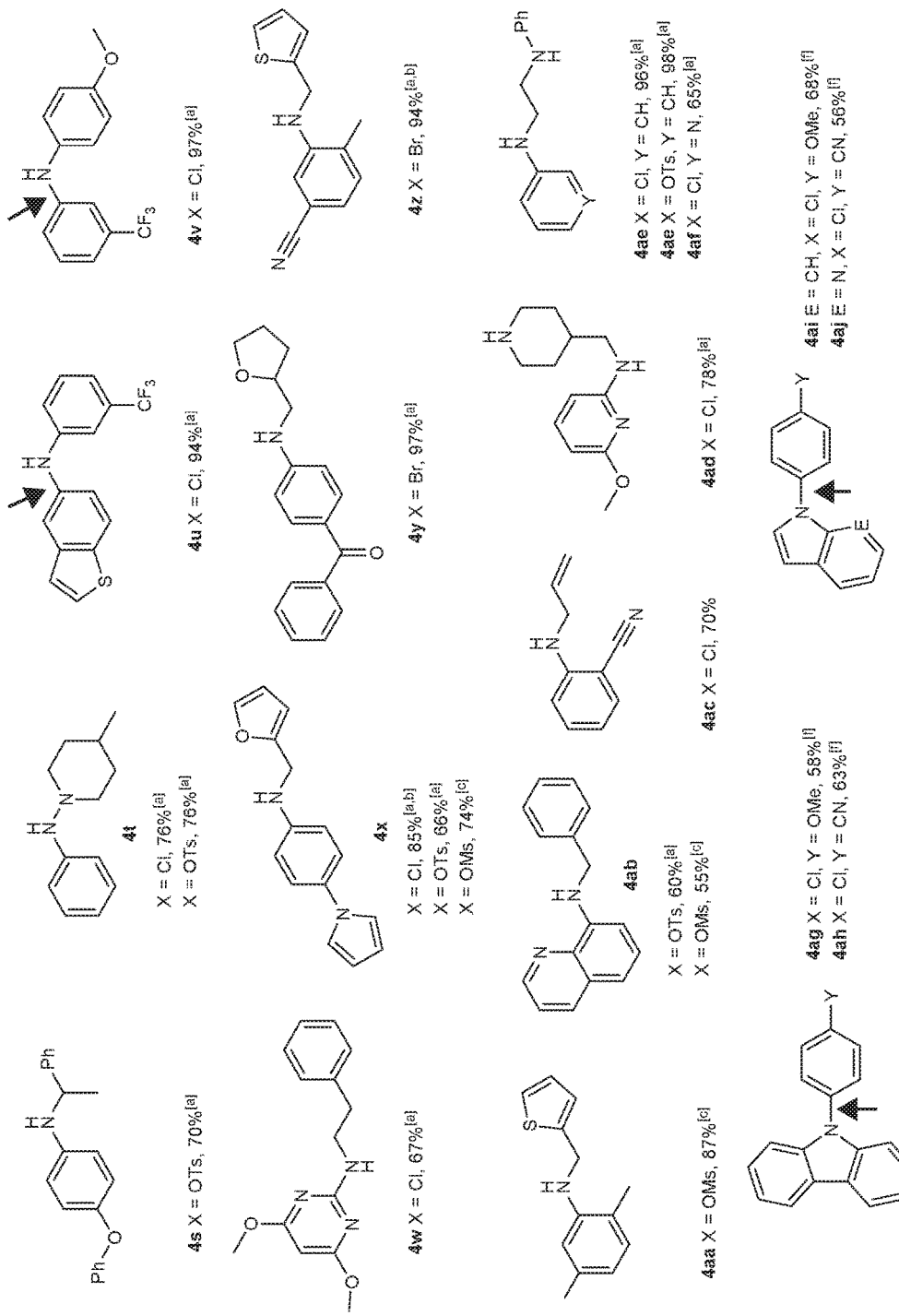
FIG. 7 is a list of exemplary chemical products synthesized using a variety of starting materials, and catalyzed using a pre-catalyst according to the present disclosure.
Figure 8:
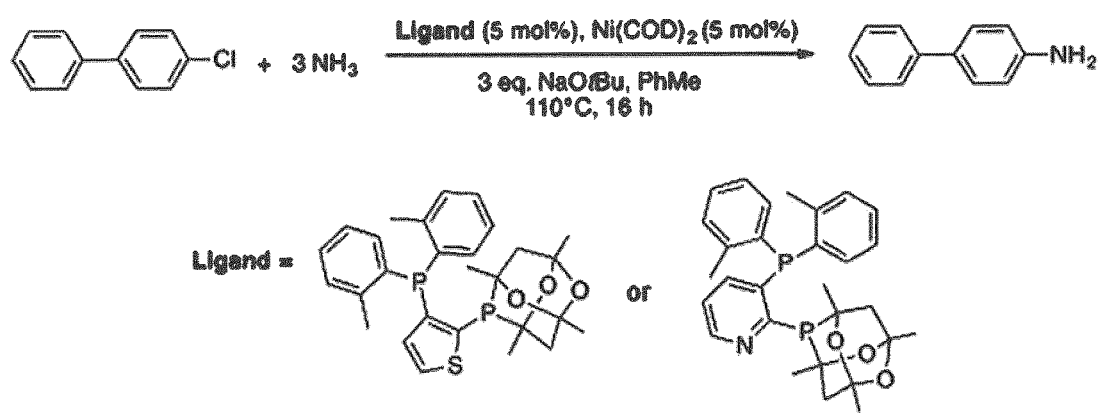
FIG. 8 is an illustration of a synthetic scheme which may be used to form a C(sp2)-N bond using ligands according to the present disclosure which generate, in situ, catalysts according to the present disclosure.

Summary of Reaction Products Made Using One or More of the Above Exemplary Protocols FIG. 4-7 illustrate the compounds which have been made using various combinations of different aryl halides, heteroaryl halides, aryl pseudohalides, and heteroaryl pseudohalides with different amine-containing compounds. FIG. 7 identifies, where necessary, the formed C(sp2)-N bonds using arrows. The reactions used to form the compounds shown in FIGS. 4-7 used the pre-catalyst shown in Formula (VIII) (1-5 mol %). FIG. 8 illustrates a reaction used to generate an aryl amine using a catalyst that is generated in situ from the mixture of a compound of Formula (VI) or (VII) and $Ni(COD)_2$.

Figure 4:
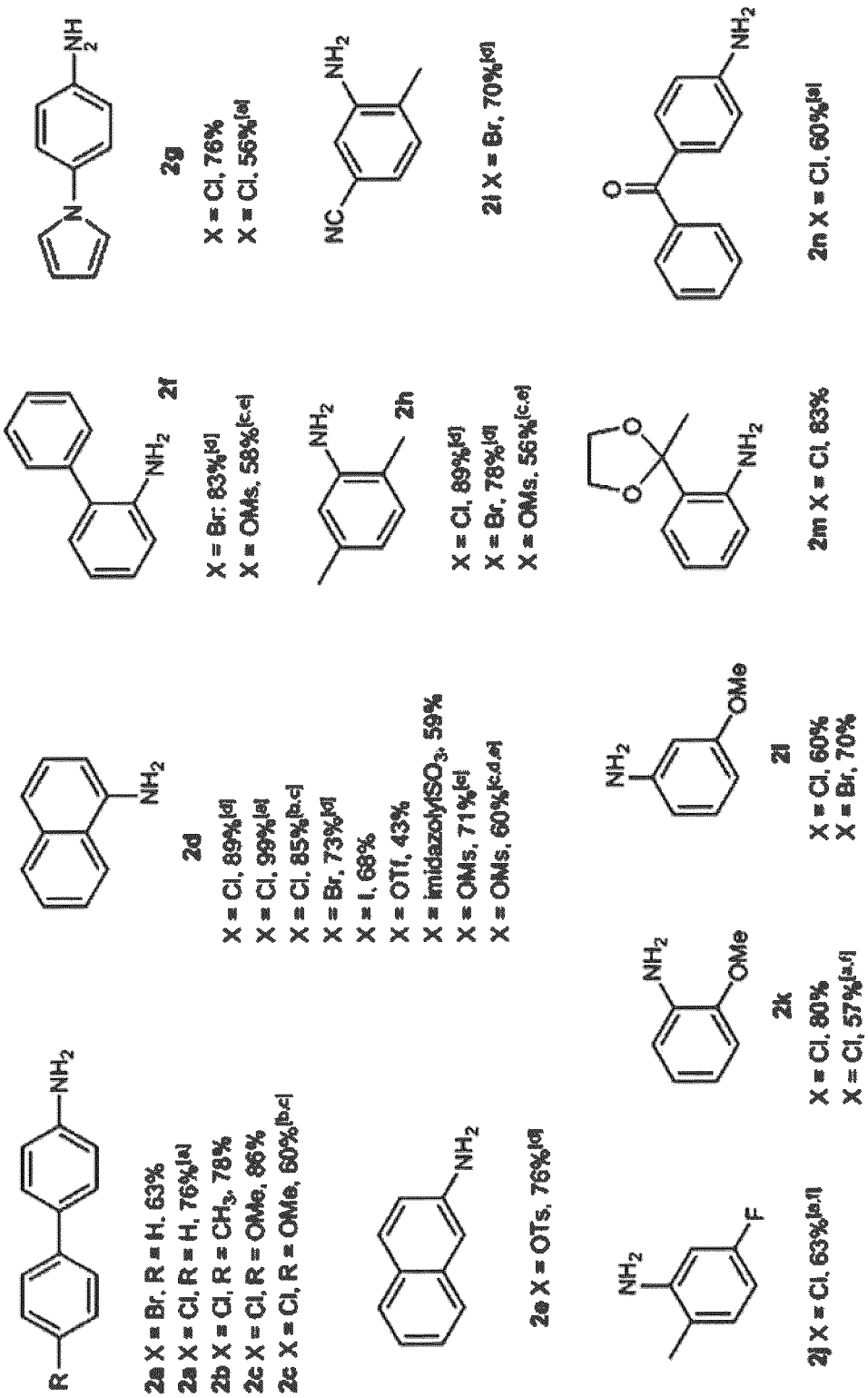
FIG. 4 is a list of exemplary chemical products synthesized using a variety of starting materials, and catalyzed using a pre-catalyst according to the present disclosure.

The reactions used to form the compounds shown in FIGS. 4 and 5 used MOtBu (M=Li or Na; 1.5-2.0 equiv), $NH_3$ (from 0.5 M solutions in 1,4-dioxane; 3-8.3 equiv), and performed the reactions in toluene for 16 h (unoptimized). Yields of isolated products are shown. Additional details with regard to FIGS. 4 and 5 include: [a] 110-160° C. for 5-30 minutes under microwave conditions using $NH_4OAc$ (5 equiv) and NaOtBu (6.5 equiv) in CPME; [b] conducted using gaseous ammonia (114 psi initial pressure); [c] yield on the basis of $^1H$ NMR data relative to ferrocene as an internal standard; [d] 25° C.; [e] $K_3PO_4$ (6 equiv) used as base at 110° C. without toluene co-solvent; and [f] isolated as the N-tosylated derivative.

The reactions used to form the compounds shown in FIGS. 6 and 7 used NaOtBu (1.5 equiv), amine (1.1 equiv), and performed the reactions in toluene for 16 h (unoptimized). Yields of isolated products are shown. Additional details with regard to FIGS. 6 and 7 include: [a] 25° C.; [b] 1 mol % the pre-catalyst shown in Formula (VIII); [c] $K_3PO_4$ (6 equiv) used as base, in CPME at 110° C.; [d] 110-140° C. for 5-30 minutes under microwave conditions using NaOtBu (6.5 equiv) and MeNH₃Cl or EtNH₃Cl (5 equiv) in CPME; [e] 3-7 equiv amine; and [f] 10 mol % the pre-catalyst shown in Formula (VIII), NaOtBu (3 equiv), amine (1 equiv) in 1,4-dioxane at 110° C.

The reactions used to form the compound shown in FIG. 8 used NaOtBu (3 equiv), amine (3 equiv), the compound of Formula (VI) or (VII) (5 mol %), Ni(COD)₂ (5 mol %), and 4-chlorobiphenyl, and performed the reactions in toluene for 16 h (unoptimized). Yields of 4-aminobiphenyl was 80% when using the compound of Formula (VI) and 60% when using the compound of Formula (VII).

4-aminobiphenyl monoarylation products (2a-c) were isolated in synthetically useful yields, as were 1- or 2-naphthylamines (2d,e) derived from an unprecedentedly wide array of 1- or 2-, halo- or pseudohalo-, naphthalenes. Electrophiles featuring or lacking ortho-substitution were also accommodated, including variants incorporating pyrrole, cyano, fluoro, methoxy, dioxolane, ketone, and alkene functionalities (2f-o). Given the importance of biologically active anilines and heteroanalines in pharmaceutical chemistry, ammonia monoarylations reactions were tested employing aryl and heteroaryl, halide and pseudohalide, electrophiles. Quinoline, isoquinoline, quinaldine, pyrimidine, quinoxaline, quinazoline, benzothiophene, and benzothiazole core structures each proved compatible in this chemistry (2p-y). Notably, the quinazoline identified as compound "2x" represents the core structure found within a series of commercialized drugs, including doxazosin which is employed for the treatment of symptoms associated with benign prostatic hyperplasia. Moreover, the quinoline identified as compound "2y" (tacrine) has been used as a cholinesterase inhibitor for the treatment of Alzheimer's disease, while 3-aminoestrone (identified as compound "2z") has been identified as a key synthon for the construction of non-natural C-18 steroids for use in the treatment of prostate and breast cancers.

The remarkable ability of the pre-catalyst shown in Formula (VIII) to catalyze room temperature ammonia monoarylations is evidenced from compounds 2d-f,h,i, covering chloride, bromide, tosylate, and mesylate electrophiles. Furthermore, the ability to conduct such room temperature ammonia monoarylation reactions on gram-scale was confirmed in the reaction of 1-chloronaphthalene with ammonia leading to 2d (2 mol % pre-catalyst shown in Formula (VIII), 2.285 g, 76% isolated yield). The monoarylation of ammonia using 1-chloronaphthalene was found to be complete (>90% conversion to 2d on the basis of GC data) after only 15 minutes when using 5 mol % of the pre-catalyst shown in Formula (VIII), thereby underscoring the highly active nature of the pre-catalyst shown in Formula (VIII) under room temperature conditions.

While no loss in catalytic activity was observed in the monoarylation of ammonia using 1-chloronaphthalene when the solid reaction components including the pre-catalyst shown in Formula (VIII) were handled in air, followed by delivery of the ammonia stock solution on the benchtop within a nitrogen-purged glove-bag, analogous reactions conducted under an atmosphere of air were unsuccessful.

The first examples of ammonia monoarylation employing aryl mesylates and heteroaryl mesylates (2d,f,h,r) involving any catalyst system are also reported. The ability of the pre-catalyst shown in Formula (VIII) to function effectively both when using high pressures of gaseous ammonia (2c,d,s,u,v,x), and alternatively ammonium acetate under microwave reaction conditions at elevated reaction temperatures (2a,d,g,j,k,n,o,s), is unique among all previously reported catalyst systems for ammonia monoarylation.

Primary and secondary alkylamines represent an important yet relatively challenging class of substrates in $C(sp^2)$-N cross-coupling chemistry. The pre-catalyst shown in Formula (VIII) may be used in reactions where the amine-containing compound is a primary or secondary alkylamine. As represented by the synthesized compounds shown in FIGS. 6 and 7, a diversity of electron-rich and electron-poor aryl halides, heteroaryl halides, aryl pseudohalides, and heteroaryl pseudohalides, were successfully cross-coupled with linear and branched primary alkylamines featuring in some cases heterocyclic addenda, as well as a hydrazine derivative and primary anilines.

Twenty nine of the reported entries proceeded efficiently at room temperature, covering chloride, bromide and tosylate electrophiles. The gram-scale cross-coupling of 1-chloronaphthalene and octylamine at room temperature leading to 4a was also achieved (3 mol % of the pre-catalyst shown in Formula (VIII), 2.703 g, 90% isolated yield). Included in the substrate scope are the first examples of nickel-catalyzed primary alkylamine monoarylation employing aryl mesylates and heteroaryl mesylates (4a,x,aa,ab).

A $C(sp^2)$-N cross-coupling reaction employing the pre-catalyst shown in Formula (VIII) and chiral amines may be conducted without racemization, as illustrated by the room-temperature cross-coupling of racemic and separately enantiopure α-methylbenzylamine leading to 4s. ¹H NMR analysis, employing a europium chiral shift reagent, of the 4s product thus formed indicated the absence of racemization when using enantiopure α-methylbenzylamine.

Reactions involving small nucleophilic reagents such as methylamine and ethylamine employing commercial stock solutions of these amines, or alternatively alkylammonium salts under microwave conditions, proceeded successfully.

The formation of the pinacolborane derivative 4o demonstrated the feasibility of conducting $C(sp^2)$-N cross-coupling reactions using the pre-catalyst shown in Formula (VIII) in the presence of a potentially reactive pinacolborane moiety, which may be exploited subsequently in an orthogonal cross-coupling step.

The preferred arylation of a primary alkylamine fragment in the presence of contending secondary amine groups by the pre-catalyst shown in Formula (VIII) was demonstrated in the chemoselective formation of 4ad-af.

Carbazole, indole, and 7-azaindole were successfully N-arylated using the pre-catalyst shown in Formula (VIII), employing electron-rich and electron-poor electrophiles, affording 4ag-aj.

The successful $C(sp^2)$-N cross-coupling of ammonia, primary alkylamines, and indoles by use of the pre-catalyst shown in Formula (VIII) is particularly remarkable, given that these compounds span more than twenty orders of magnitude in terms of NH acidity.

Methods

General Considerations.

Unless otherwise stated, all reactions were setup inside a nitrogen-filled inert atmosphere glovebox, and were worked up in air using benchtop procedures. Toluene was deoxygenated by sparging with nitrogen followed by passage through a double column solvent purification system packed with alumina and copper-Q5 reactant, and storage over activated 4 Å molecular sieves. CPME was degassed by use of three repeated freeze-pump-thaw cycles and was stored over activated 4 Å molecular sieves. 1,4-Dioxane used in General Procedure I (GPI) was dried over Na/benzophenone followed by distillation under a nitrogen atmosphere. Otherwise, all reagents, solvents and materials were used as received from commercial sources. Column chromatography was carried out using Silicycle SiliaFlash 60 silica (particle size 40-63 μm; 230-400 mesh) or using neutral alumina (150 mesh; Brockmann-III; activated), as indicated. Preparatory TLC was carried out on Silicycle plates (TLG-R1001B-341, silica glass-backed TLC Extra Hard Layer, 60 angstrom, thickness 1 mm, indicator F-254). Unless stated NMR spectra were recorded at 300 K in $CDCl_3$ with chemical shifts expressed in parts per million (ppm) using the residual $CHCl_3$ solvent signal ($^1H$, 7.26 ppm; $^{13}C$, 77 ppm) as an internal reference, or $H_3PO_4$ as an external reference ($^{31}P$, 0.00 ppm). Splitting patterns are indicated as follows: br, broad; s, singlet; d, doublet; m, multiplet, with all coupling constants (J) reported in Hertz (Hz). In some cases fewer than expected independent $^{13}C$ NMR resonances were observed despite prolonged acquisition times. For NMR analysis of the compounds in this article, see the Supplementary Methods and Supplementary FIGS. 1-142. Mass spectra were obtained using ion trap (ESI) instruments operating in positive mode, and GC data were obtained on an instrument equipped with a SGE BP-5 column (30 m, 0.25 mm i.d.).

Synthesis of 2a.

Following the protocol of GPA: (1.8 mmol ammonia, 3 mol % PAdDalPhosNi(o-tol)Cl (P1), 2 eq. LiOtBu) Purified by column chromatography (10:1; hexanes/EtOAc) to yield 2a as a beige yellow solid in 63% yield from the corresponding bromide. $^1H$ NMR (300 MHz, $CDCl_3$): δ 7.58-7.56 (m, 2H), 7.46-7.40 (m, 4H), 7.32-7.28 (m, 1H), 6.80-6.77 (m, 2H), 3.72 (br s, 2H); $^{13}C\{^1H\}$ NMR (75.5 MHz, $CDCl_3$): δ 145.8, 141.2, 131.6, 128.7, 128.0, 126.4, 126.3, 115.4. Agrees with data previously reported in the literature. Following the protocol of GPD: (0.02 mmol ammonium acetate, 2 mol % PAdDalPhosNi(o-tol)Cl (P1), 140° C., 5 minutes) compound 2a was isolated in 76% yield from the corresponding chloride.

Synthesis of 2b.

Following the protocol of GPA: (1.8 mmol ammonia, 4 mol % PAdDalPhosNi(o-tol)Cl (P1)) Purified by column chromatography (5:1, hexanes/EtOAc) to yield 2b as a yellow solid in 78% yield from the corresponding chloride. $^1H$ NMR (500 MHz, $CDCl_3$): δ δ 7.48-7.43 (m, 4H), 7.25-7.23 (m, 2H), 6.79-6.78 (m, 2H), 3.89 (br s, 2H), 2.43 (s, 3H); $^{13}C\{^1H\}$ NMR (125.8 MHz, $CDCl_3$): δ 145.8, 138.5, 136.1, 131.9, 129.7, 128.0, 126.5, 115.6, 21.2. Agrees with data previously reported in the literature.

Synthesis of 2c.

Following the protocol of GPA: (1.8 mmol ammonia, 4 mol % PAdDalPhosNi(o-tol)Cl (P1)) Purified by column chromatography (5:1, hexanes/EtOAc) to yield as a yellow solid in 86% yield from the corresponding chloride. $^1H$ NMR (500 MHz, $CDCl_3$): δ 7.50-7.48 (m, 2H), 7.40-7.39 (m, 2H), 6.99-6.97 (m, 2H), 6.79-6.78 (m, 2H), 3.87 (s, 3H), 3.73 (br s, 2H); $^{13}C\{^1H\}$ NMR (125.8 MHz, $CDCl_3$): δ 158.7, 145.5, 134.1, 131.6, 127.8, 127.6, 115.7, 114.3, 55.6. Agrees with data previously reported in the literature. Following the protocol of GPE compound 2c was generated in 60% yield from the corresponding chloride on the basis of NMR integration using ferrocene as an internal standard.

Synthesis of 2d.

Following the protocol of GPA, PAdDalPhosNi(o-tol)Cl (P1) (2 mol %, 0.42 mmol, 290 mg), 1-chloronapthalene (1 equiv, 21 mmol, 2.85 mL), NaOtBu (2 equiv, 42 mmol, 4.03 g), ammonia (0.5M in dioxane, 3 equiv, 63 mmol, 126 mL) and toluene (224 mL) were added to an oven dried 500 mL round bottom equipped with a magnetic stir bar. The reaction flask was sealed with a septum and stirring was initiated at room temperature. After 16 h (unoptimized), the solvent was removed with the aid of a rotary evaporator. The crude residue was dissolved in EtOAc (150 mL), washed with distilled water (2×150 mL), and once with brine (150 mL). The organic layer was dried over anhydrous $Na_2SO_4$, filtered, and concentrated with the aid of a rotary evaporator. The crude material was purified via automated column chromatography using a EtOAc:hexanes gradient 0-40% EtOAc, giving 2d (2.285 g, 76% yield). Following the protocol of GPD: (5 mmol ammonium acetate, 1 mol % PAdDalPhosNi(o-tol)Cl (P1), 110° C., 5 minutes) compound 2d was isolated in 99% yield from the corresponding chloride. Following the protocol of GPE: compound 2d was generated in 85% yield from the corresponding chloride on the basis of NMR integration using ferrocene as an internal standard. Following the protocol of GPA: (3.0 mmol ammonia, 3 mol % PAdDalPhosNi(o-tol)Cl (P1), 25° C.) compound 2d was isolated in 73% yield from the corresponding bromide. Following the protocol of GPA: (3.0 mmol ammonia, 4 mol % PAdDalPhosNi(o-tol)Cl (P1)) compound 2d was isolated in 68% yield from the corresponding iodide. Following the protocol of GPA: (4.2 mmol ammonia, 4 mol % PAdDalPhosNi(o-tol)Cl (P1)) compound 2d was isolated in 43% yield from the corresponding triflate. Following the protocol of GPA: (4.2 mmol ammonia, 5 mol % PAdDalPhosNi(o-tol)Cl (P1), 2 equiv LiOtBu) compound 2d was isolated in 59% yield from the corresponding imidazolyl sulfonate. Following the protocol of GPC: (5 mol % PAdDalPhosNi(o-tol)Cl (P1), 8.3 equiv ammonia) compound 2d was isolated in 71% yield from the corresponding mesylate. Following the protocol of GPC: (5 mol % PAdDalPhosNi(o-tol)Cl (P1), 4.2 equiv ammonia, [aryl mesylate]=0.12 M) compound 2d was generated in 60% yield at 25° C. from the corresponding mesylate on the basis of NMR integration using ferrocene as an internal standard.

Synthesis of 2e.

Following the protocol of GPA: (3.0 mmol ammonia, 2 mol % PAdDalPhosNi(o-tol)Cl (P1), 25° C.) Purified by column chromatography (5:1, hexanes/EtOAc) to yield 2e as a purple solid in 76% yield from the corresponding tosylate. $^1H$ NMR (500 MHz, $CDCl_3$): δ 7.77-7.69 (m, 2H), 7.64-7.62 (d, 1H), 7.42-7.39 (m, 1H), 7.28-7.25 (m, 1H), 7.03-7.02 (m, 1H), 6.99-6.98 (m, 1H), 3.88 (br s, 2H); $^{13}C\{^1H\}$ NMR (125.8 MHz, $CDCl_3$): δ 144.2, 135.1, 129.4, 128.2, 127.9, 126.7, 126.0, 122.7, 118.4, 108.9. Agrees with data previously reported in the literature.

Synthesis of 2f.

Following the protocol of GPA: (3.0 mmol ammonia, 3 mol % PAdDalPhosNi(o-tol)Cl (P1), 25° C.) Purified by column chromatography (10:1, hexanes/EtOAc) to yield 2f as a solid in 83% yield from the corresponding bromide. $^1H$ NMR (300 MHz, $CDCl_3$): δ 7.48-7.47 (m, 4H), 7.39-7.33 (m, 1H), 7.19-7.14 (m, 2H), 6.88-6.78 (m, 2H), 3.78 (br s, 2H); $^{13}C\{^1H\}$ NMR (125.8 MHz, $CDCl_3$): δ 143.7, 139.8, 130.7, 129.3, 129.0, 128.7, 127.9, 127.4, 118.9, 115.8. Agrees with data previously reported in the literature. Following the protocol of GPC: (5 mol % PAdDalPhosNi(o-tol)Cl (P1), 8.3 equiv ammonia) compound 2f was generated in 58% yield from the corresponding mesylate on the basis of NMR integration using ferrocene as an internal standard.

Synthesis of 2g.

Following the protocol of GPA: (3.0 mmol ammonia, 4 mol % PAdDalPhosNi(o-tol)Cl (P1), 2 equiv LiOtBu) Purified by column chromatography (10:1, hexanes/EtOAc) to yield 2g as a light brown solid in 76% yield from the corresponding chloride. $^1H$ NMR (500 MHz, $CDCl_3$): δ 7.23-7.22 (m, 2H), 7.02-7.01 (m, 2H), 6.77-6.75 (m, 2H), 6.35-6.34 (m, 2H), 3.76 (br s, 2H); $^{13}C\{^1H\}$ NMR (125.8

MHz, CDCl$_3$): δ 144.7, 133.1, 122.6, 119.9, 115.9, 109.7. Agrees with data previously reported in the literature. Following the protocol of GPD: (2 mol % PAdDalPhosNi(o-tol)Cl (P1), 140° C., 20 minutes) compound 2g was isolated in 56% yield from the corresponding chloride.

Synthesis of 2h.

Following the protocol of GPA: (3.0 mmol ammonia, 4 mol % PAdDalPhosNi(o-tol)Cl (P1), 25° C.) Purified by column chromatography (10:1, hexanes/EtOAc) to yield 2h as a colorless oil in 89% yield from the corresponding chloride. $^1$H NMR (500 MHz, CDCl$_3$): δ 7.01 (d, J=7.5 Hz, 1H), 6.62 (d, J=8.0 Hz, 1H), 6.57 (s, 1H), 3.61 (br s, 2H), 2.33 (s, 3H), 2.20 (s, 3H); $^{13}$C{$^1$H} NMR (125.8 MHz, CDCl$_3$): δ 144.6, 136.8, 130.5, 119.5, 115.9, 21.2, 17.0. Agrees with data previously reported in the literature. Following the protocol of GPA: (3.0 mmol ammonia, 4 mol % PAdDalPhosNi(o-tol)Cl (P1), 25° C.) compound 2h was isolated as a colourless oil in 78% yield from the corresponding bromide. Following the protocol of GPC: (5 mol % PAdDalPhosNi(o-tol)Cl (P1), 8.3 equiv ammonia) compound 2h was generated in 58% yield from the corresponding mesylate on the basis of NMR integration using ferrocene as an internal standard.

Synthesis of 2i.

Following the protocol of GPA: (3.0 mmol ammonia, 3 mol % PAdDalPhosNi(o-tol)Cl (P1), 25° C.) Purified by extraction with 1.0 M aqueous HCl to yield 2i as a solid in 70% yield from the corresponding bromide. $^1$H NMR (300 MHz, CDCl$_3$): δ 7.14-7.12 (m, 1H), 7.01-7.00 (m, 1H), 6.93 (s, 1H), 3.82 (br s, 2H), 2.22 (s, 3H); $^{13}$C{$^1$H} NMR (125.8 MHz, CDCl$_3$): δ 145.2, 131.3, 127.9, 122.5, 119.6, 117.5, 110.6, 17.9. Data agrees with commercial source material (CAS: 60710-80-7).

Synthesis of 2j.

Following the protocol of GPD: (5 mmol ammonium acetate, 5 mol % PAdDalPhosNi(o-tol)Cl (P1), 140° C., 20 minutes). The crude product was tosylated using a literature procedurelto yield 2j as a white solid in 63% yield. $^1$H NMR (300 MHz, CDCl$_3$): δ 7.70-7.65 (m, 2H), 7.28-7.25 (m, 2H), 7.19-7.15 (m, 1H), 7.06-7.01 (m, 1H), 6.80-6.73 (m, 1H), 6.57 (br s, 1H), 2.41 (s, 3H), 1.99 (s. 3H); $^{13}$C{$^1$H} NMR (75.5 MHz, CDCl$_3$): δ 161.3 (J$_{CF}$=244.0 Hz), 144.1, 136.4, 135.6 (J$_{CF}$=10.4 Hz), 129.7, 127.1, 125.2 (J$_{CF}$=3.1 Hz), 112.3 (J$_{CF}$=21.1 Hz), 110.1 (J$_{CF}$=25.3 Hz), 21.5, 16.8; HRMS m/z ESI$^+$ found 302.0621 [M+Na]$^+$ calculated for C$_{14}$H$_{14}$FNO$_2$SNa 302.0627.

Synthesis of 2k.

Following the protocol of GPA: (3.0 mmol ammonia, 3 mol % PAdDalPhosNi(o-tol)Cl (P1)) Purified by extraction with 1.0 M aqueous HCl to yield 2k as a brown oil in 80% yield (ca. 90% purity) from the corresponding chloride. $^1$H NMR (300 MHz, CDCl$_3$): δ 6.85-6.76 (m, 4H), 3.96-3.89 (m, 5H); $^{13}$C{$^1$H} NMR (125.8 MHz, CDCl$_3$): δ 147.6, 136.2, 121.3, 118.8, 115.3, 110.7, 55.8. Agrees with data previously reported in the literature. Following the protocol of GPD: (5 mmol ammonium acetate, 5 mol % PAdDalPhosNi(o-tol)Cl (P1), 160° C., 30 minutes) The crude product was tosylated using a literature procedure to yield 2k as a brown oil in 57% yield. $^1$H NMR (300 MHz, CDCl$_3$): δ 7.68-7.65 (m, 2H), 7.55-7.52 (m, 1H), 7.22-7.19 (m, 2H), 7.07-7.01 (m, 2H), 6.94-6.88 (m, 1H), 6.76-6.73 (m, 1H), 3.66 (s, 3H), 2.37 (s. 3H); $^{13}$C{$^1$H} NMR (75.5 MHz, CDCl$_3$): δ 149.4, 143.6, 136.4, 129.3, 127.3, 126.1, 125.2, 121.1, 121.0, 110.6, 55.6, 21.5.

Synthesis of 2l.

Following the protocol of GPA: (1.8 mmol ammonia, 3 mol % PAdDalPhosNi(o-tol)Cl (P1)) Purified by extraction with 1.0 M aqueous HCl to yield 2l as a brown oil in 60% yield (ca. 90% purity) from the corresponding chloride. $^1$H NMR (300 MHz, CDCl$_3$): δ 7.12-7.09 (m, 1H), 6.39-6.33 (m, 2H), 6.29 (s, 1H), 3.80 (s, 3H), 3.74 (br s, 2H); $^{13}$C{$^1$H} NMR (125.8 MHz, CDCl$_3$): δ 160.9, 147.7, 130.3, 108.3, 104.4, 101.4, 55.3. Agrees with data previously reported in the literature. Following the protocol of GPA (3.0 mmol ammonia, 3 mol % PAdDalPhosNi(o-tol)Cl (P1)): Purified by extraction with 1.0 M aqueous HCl to yield compound 2l in 70% yield (ca. 90% purity) from the corresponding bromide.

Synthesis of 2m.

Following the protocol of GPA: (5 mmol ammonia, 5 mol % PAdDalPhosNi(o-tol)Cl (P1)) Purified by preparatory TLC (10:1 EtOAc/NEt$_3$) to yield 2m as a yellow oil in 83% yield from the corresponding chloride. $^1$H NMR (500 MHz, CDCl$_3$): 7.39-7.37 (m, 1H), 7.14-7.11 (m, 1H), 6.77-6.74 (m, 1H), 6.68-6.66 (m, 1H), 4.32 (br s, 2H), 4.12-4.05 (m, 2H), 3.90-3.83 (m, 2H), 1.75 (s, 3H); $^{13}$C{$^1$H} NMR (125.8 MHz, CDCl$_3$): 144.7, 129.5, 127.0, 126.3, 118.2, 117.2, 109.9, 64.5, 24.9; HRMS m/z ESI$^+$ found: 180.1024 [M+H]$^+$ calculated for C$_{10}$H$_{14}$NO$_2$ 180.1019.

Synthesis of 2n.

Following the protocol of GPD: (5 mmol ammonium acetate, 5 mol % PAdDalPhosNi(o-tol)Cl (P1), 140° C., 5 minutes). Purified by column chromatography (0% EtOAc/100% hexanes to 50/50% EtOAc/hexanes gradient) to yield 2n as a white solid in 60% yield from the corresponding chloride. $^1$H NMR (300 MHz, DMSO): δ 7.57-7.62 (m, 3H), 7.54-7.56 (m, 1H), 7.51-7.52 (m, 2H), 7.48-7.50 (m, 1H), 6.57-6.64 (m, 2H), 6.14 (br s, 2H); $^{13}$C{$^1$H} NMR (75.5 MHz, DMSO); δ 193.3, 153.7, 139.0, 132.5, 130.9, 128.7, 128.1, 123.6, 112.5. Agrees with data previously reported in the literature.

Synthesis of 2o.

Following the protocol of GPD: (5 mmol ammonium acetate, 3 mol % PAdDalPhosNi(o-tol)Cl (P1), 140° C., 20 minutes). Purified by column chromatography (0% EtOAc/100% hexanes to 30/70% EtOAc/hexanes gradient) to yield 2o as a brown oil in 65% yield from the corresponding chloride. $^1$H NMR (300 MHz, CDCl$_3$): δ 7.30-7.36 (m, 2H), 6.63-6.70 (m, 2H), 5.25-5.29 (m, 1H), 4.92-4.97 (m, 1H), 3.68 (br s, 2H), 2.13 (s, 3H); $^{13}$C{$^1$H} NMR (75.5 MHz, CDCl$_3$): δ 145.8, 142.7, 131.6, 126.4, 114.7, 109.3, 21.8. Agrees with data previously reported in the literature.

Synthesis of 2p.

Following the protocol of GPB: Purified by column chromatography (10:1:0.1, hexanes/EtOAc/NHiPr$_2$) to yield 2p as a light brown solid in 81% yield from the corresponding bromide. $^1$H NMR (500 MHz, CDCl$_3$): δ 8.69-8.68 (m, 1H), 7.93 (t, J=9 Hz, 2H), 7.31-7.28 (m, 1H), 7.20-7.18 (m, 1H), 6.93-6.92 (m, 1H) 4.00 (br s, 2H); $^{13}$C{$^1$H} NMR (125.8 MHz, CDCl$_3$): δ 147.1, 144.8, 143.7, 134.0, 130.8, 130.0, 121.8, 121.6, 107.6. Agrees with data previously reported in the literature.

Synthesis of 2q.

Following the protocol of GPB: Purified by preparatory TLC (7:2:1, hexanes/EtOAc/NHiPr$_2$) to yield 2q as a white solid in 82% yield from the corresponding chloride. $^1$H NMR (500 MHz, CDCl$_3$): δ 8.79 (s, 1H), 8.08 (s, 1H) 7.96 (d, J=8.2 Hz, 1H), 7.85 (d, 8.4 Hz, 1H), 7.73-7.72 (m, 1H), 4.12 (br s, 2H); $^{13}$C{$^1$H} NMR (125.8 MHz, CDCl$_3$): δ 143.7, 136.9, 129.3, 128.9, 128.6, 128.1, 127.3, 126.4, 120.2. Agrees with data previously reported in the literature.

Synthesis of 2r.

Following the protocol of GPC: Purified by column chromatography (50% DCM/hexanes to 10% NEt$_3$/hexanes)

followed by an acidic work up with ethyl acetate, 1 M aqueous HCl and distilled water. The organic fractions were combined, dried over $Na_2SO_4$ and concentrated under reduced pressure to yield 2r as an orange oil in 53% yield from the corresponding mesylate. $^1$H NMR (500 MHz, CDCl$_3$): δ 8.81-8.79 (m, 1H), 8.11-8.10 (m, 1H), 7.41-7.36 (m, 2H), 7.20-7.18 (m, 1H), 6.98-6.96 (m, 1H), 5.02 (br s, 2H); $^{13}$C{$^1$H} NMR (125.8 MHz, CDCl$_3$): δ 147.6, 144.2, 138.7, 136.2, 129.1, 127.6, 121.5, 116.3, 110.2. Agrees with data previously reported in the literature.

Synthesis of 2s.

Following the protocol of GPE: Purified by column chromatography (7:2:1, hexanes/EtOAc/NHiPr$_2$) to yield 2s as an light yellow solid in 87% yield from the corresponding chloride. $^1$H NMR (500 MHz, CDCl$_3$): δ 7.92 (d, J=8.5 Hz, 1H), 7.72-7.70 (m, 1H), 7.63-7.59 (m, 1H), 7.40-7.36 (m, 1H), 6.50 (s, 1H), 4.68 (br s, 2H), 2.58 (s, 3H); $^{13}$C{$^1$H} NMR (125.8 MHz, CDCl$_3$): δ 159.5, 149.8, 18.9, 129.6, 129.3, 124.3, 120.2, 117.6, 25.5. Agrees with data previously reported in the literature. Following the protocol of GPD: (0.5 mmol ammonium acetate, 1 mol % PAdDalPhosNi(o-tol)Cl (P1), 140° C., 5 minutes) compound 2s was isolated in 78% yield from the corresponding chloride.

Synthesis of 2t.

Following the protocol of GPB: Purified by preparatory TLC (10% NHiPr$_2$/hexanes) to yield 2t as a white solid in 71% yield from the corresponding chloride. $^1$H NMR (500 MHz, CDCl$_3$): δ 5.49 (s, 1H), 4.96 (br s, 2H), 3.87 (s, 6H); $^{13}$C{$^1$H} NMR (125.8 MHz, CDCl$_3$): δ 172.7, 162.5, 79.9, 53.9. Agrees with data previously reported in the literature.

Synthesis of 2u.

Following the protocol of GPE: Purified by column chromatography (8:2:0.2, hexanes/EtOAc/NHiPr$_2$) to yield 2u as a yellow solid in 76% yield from the corresponding chloride. $^1$H NMR (500 MHz, CDCl$_3$): δ 8.33 (s, 1H), 7.92 (d, J=9.6 Hz, 1H), 7.67-7.66 (m, 1H), 7.62-7.59 (m, 1H), 7.46-7.43 (m, 1H), 7.26 (s, 1H), 4.93 (s, 2H); $^{13}$C{$^1$H} NMR (125.8 MHz, CDCl$_3$): δ 152:1, 141.7, 138.1, 137.9, 130.7, 129.3, 126.5, 125.6. Agrees with data previously reported in the literature.

Synthesis of 2v.

Following the protocol of GPE: Purified by column chromatography (9:1:0.1, hexanes/EtOAc/NHiPr$_2$) to yield 2v as a white solid in 68% yield from the corresponding chloride. $^1$H NMR (500 MHz, CDCl$_3$): δ 7.67 (d, J=8.6 Hz, 1H), 7.42 (d, J=5.4 Hz, 1H), 7.19 (d, J=5.4 Hz, 1H), 7.15-7.14 (m, 1H), 6.83-6.81 (m, 1H), 3.73 (s, 2H); $^{13}$C{$^1$H} NMR (125.8 MHz, CDCl$_3$): δ 143.8, 141.1, 130.7, 127.3, 123.3, 123.2, 115.1, 108.5. Agrees with data previously reported in the literature.

Synthesis of 2w.

Following the protocol of GPB: (5 mol % PAdDalPhosNi (o-tol)Cl (P1)) Purified by column chromatography (5:5:0.1, hexanes/EtOAc/NHiPr$_2$) to yield 2w as a white solid in 77% yield from the corresponding chloride. $^1$H NMR (500 MHz, CDCl$_3$): δ 7.58 (d, J=8.5 Hz, 1H), 7.28-7.27 (m, 1H), 6.80-6.67 (m, 1H), 3.82 (br s, 2H), 2.82 (s, 3H); $^{13}$C{$^1$H} NMR (125.8 MHz, CDCl$_3$): δ 168.0, 155.1, 145.5, 125.7, 121.9, 114.7, 107.7, 20.3. Agrees with data previously reported in the literature.

Synthesis of 2x.

Following the protocol of GPE: Purified by column chromatography (5:5:1, hexanes/EtOAc/NHiPr$_2$) to yield 2x as a beige-yellow solid in 90% yield from the corresponding chloride. $^1$H NMR (500 MHz, DMSO): δ 8.25 (s, 1H), 7.67 (s, 1H), 7.46 (br s, 2H), 7.06 (s, 1H), 3.89 (s, 3H), 3.88 (s, 3H); $^{13}$C{$^1$H} NMR (125.8 MHz, DMSO): δ 160.4, 154.0, 153.8, 148.1, 146.6, 108.0, 106.7, 102.9, 56.1, 55.6; Agrees with data previously reported in the literature.

Synthesis of 2y.

Following the protocol of GPB: (5 mol % PAdDalPhosNi (o-tol)Cl (P1)) Purified by column chromatography (6:4:1, EtOAc/hexanes/NHiPr$_2$) to yield 2y as a beige solid in 87% yield from the corresponding chloride. $^1$H NMR (500 MHz, CDCl$_3$): δ 7.91-7.88 (m, 1H), 7.72-7.69 (m, 1H), 7.59-7.53 (m, 1H), 7.39-7.33 (m, 1H), 4.72 (br s, 2H), 3.05-3.01 (m, 2H), 2.63-2.59 (m, 2H), 1.99-1.88 (m, 4H); $^{13}$C{$^1$H} NMR (125.8 MHz, CDCl$_3$): δ 158.6, 146.8, 146.5, 128.8, 128.7, 124.1, 119.9, 117.3, 110.6, 34.1, 23.9, 23.0, 22.9. Agrees with data previously reported in the literature.

Synthesis of 2z.

Following the protocol of GPB: Purified by column chromatography (30% EtOAc/hexanes) to yield as a white solid in 58% yield 2z from the corresponding triflate. $^1$H NMR (500 MHz, CDCl$_3$): δ 7.12 (d, J=8.3 Hz, 1H), 6.57-6.55 (m, 1H), 6.49-6.48 (m, 1H), 3.56 (br s, 2H), 2.89-2.86 (m, 2H), 2.56-2.51 (m, 1H), 2.43-2.39 (m, 1H), 2.28-2.23 (m, 1H), 2.21-2.13 (m, 1H), 2.11-2.06 (m, 1H), 2.04-1.96 (m, 2H), 1.70-1.41 (m, 7H), 0.94 (s, 3H); $^{13}$C{$^1$H} NMR (125.8 MHz, CDCl$_3$): δ 221.2, 144.4, 137.6, 130.3, 126.4, 115.6, 113.3, 50.7, 48.3, 44.2, 38.7, 36.1, 31.8, 29.7, 26.8, 26.2, 21.8, 14.1. Agrees with data previously reported in the literature.

Synthesis of 4a.

Following the protocol of GPF: PAdDalPhosNi(o-tol)Cl (P1) (3 mol %, 0.35 mmol, 241 mg), 1-chloronaphthalene (1 equiv, 11.7 mmol, 1.60 mL), octylamine (1.1 equiv, 12.9 mmol, 2.13 mL), NaOtBu (1.5 equiv, 17.6 mmol, 1.69 g) and toluene (120 mL) were added to an oven dried 250 round bottom flask equipped with a magnetic stir bar. The reaction flask was sealed with a septum and stirring was initiated at room temperature. After 16 h (unoptimized), the solvent was removed with the aid of a rotary evaporator. The crude residue was dissolved in EtOAc (150 mL), washed with distilled water (2×150 mL), and once with brine (150 mL). The organic layer was dried over anhydrous $Na_2SO_4$, filtered, and concentrated with the aid of a rotary evaporator. The crude material was purified via automated column chromatography using a EtOAc:hexanes gradient 0-20% EtOAc, giving 4a (2.703 g, 90% yield).

Following the protocol of GPF: using 0.50 mmol 1-chloro-naphthylene, 0.55 mmol octylamine, 1 mol % PAdDalPhosNi(o-tol)Cl, at 25° C., compound 4a was isolated as a yellow oil in 96% yield. A 1% ethyl acetate/ hexanes eluent system was used for column chromatography on silica gel. $^1$H NMR (500 MHz, CDCl$_3$): δ 7.85-7.82 (m, 2H), 7.50-7.45 (m, 2H), 7.41-7.38 (m, 1H), 7.30-7.26 (m, 1H), 6.66 (d, J=8.5 Hz, 1H), 4.35 (br s, 1H), 3.32-3.30 (m, 2H), 1.85-1.80 (m, 2H), 1.57-1.51 (m, 2H), 1.45-1.35 (m, 8H) 0.96 (t, J=6.8 Hz, 3H); $^{13}$C{$^1$H} NMR (125.8 MHz, CDCl$_3$): δ 143.9, 134.6, 128.9, 126.9, 125.9, 124.8, 123.6, 120.0, 117.4, 104.5, 44.6, 32.3, 29.7, 29.6, 27.6, 22.9, 14.4. Spectral data are consistent with the literature. Following the protocol of GPF (25° C.) compound 4a was isolated as a yellow oil in 94% yield from the corresponding bromide. Following the protocol of GPH compound 4a was isolated as a yellow oil in 91% yield from the corresponding mesylate (5 mol % PAdDalPhosNi(o-tol)Cl).

Synthesis of 4b.

Following the protocol of GPD: (1.0 mmol 1-chloronaphthalene, 5.0 mmol methylammonium chloride, 1 mol % PAdDalPhosNi(o-tol)Cl, 110° C., 5 minutes). Compound 4b was isolated as a brown oil in 99% yield. $^1$H NMR (300 MHz, CDCl$_3$): δ 7.79-7.88 (m, 2H), 7.40-7.54 (m, 3H), 7.28-7.33 (m, 1H), 6.65 (d, J=7.5 Hz, 1H), 4.48 (br s, 1H), 3.05 (s, 3H); $^{13}C\{^1H\}$ (75.5 MHz, CDCl$_3$): δ 144.5, 134.2, 128.6, 126.7, 125.7, 124.7, 123.4, 119.8, 117.3, 103.8, 31.0. Spectral data are in agreement with the literature.

Synthesis of 4c.

Following the protocol of GPD: (1.0 mmol 1-chloronaphthalene, 5.0 mmol ethylammonium chloride, 1 mol % PAdDalPhosNi(o-tol)Cl, 110° C., 5 minutes): Compound 4c was isolated as a dark brown oil in 99% yield. $^1$H NMR (300 MHz, CDCl$_3$): δ 7.81-7.88 (m, 2H), 7.37-7.53 (m, 3H), 7.29 (d, J=7.9 Hz, 1H) 6.67 (d, J=6.9 Hz, 1H), 4.33 (br s, 1H), 3.37 (q, J=7.1 Hz, 2H), 1.45 (t, J=7.1, 3H); $^{13}C\{^1H\}$ (75.5 MHz, CDCl$_3$): δ 143.5, 134.3, 128.6, 126.6, 125.6, 124.6, 123.3, 119.8, 117.2, 104.3, 38.7, 14.8. Spectral data are in agreement with the literature.

Synthesis of 4d.

Following the protocol of GPG: (0.60 mmol 1-chloronaphthylene, 1.8 mmol dimethylamine, 5 mol % PAdDalPhosNi(o-tol)Cl, 110° C.) compound 4d was isolated as a brown oil in 57% yield. A 2% ethyl acetate/hexanes eluent system was used for column chromatography on silica gel. $^1$H NMR (300 MHz, CDCl$_3$): δ 8.29-8.27 (m, 1H), 7.87-7.84 (m, 1H), 7.57-7.48 (m, 3H), 7.46-7.40 (m, 1H), 7.13-7.10 (m, 1H), 2.95-2.94 (m, 6H); $^{13}C\{^1H\}$ NMR (75.5 MHz, CDCl$_3$): δ 145.7, 145.0, 143.4, 140.4, 138.2, 130.1, 122.0, 103.3, 30.5. Spectral data are in agreement with the literature.

Synthesis of 4e.

Following the protocol of GPF: (0.50 mmol 4-chloroanisole, 0.55 mmol octylamine, 5 mol % PAdDalPhosNi(o-tol)Cl, 60° C.) compound 4e was isolated as a dark yellow oil in 85% yield. A 5% ethyl acetate/hexanes eluent system was used for column chromatography on silica gel. $^1$H NMR (300 MHz, CDCl$_3$): δ 6.82-6.79 (m, 2H), 6.62-6.58 (m, 2H), 3.77 (s, 3H), 3.35 (br s, 1H), 3.11-3.06 (m, 2H), 1.67-1.58 (m, 2H), 1.46-1.31 (m, 10H), 0.91 (t, J=11.3 Hz, 3H); $^{13}C\{^1H\}$ NMR (75.5 MHz, CDCl$_3$): δ 152.0, 143.0, 114.9, 114.0, 55.9, 45.0, 31.8, 29.7, 29.4, 29.3, 27.2, 22.7, 14.1. Spectral data are in agreement with the literature. Following the protocol of GPF 4e was isolated as a dark yellow oil in 93% yield from the corresponding bromide (5 mol % PAdDalPhosNi(o-tol)Cl, 60° C.).

Synthesis of 4f.

Following the protocol of GPF: (0.50 mmol 1-chloro-4-(trifluoromethyl)benzene, 0.55 mmol octylamine, 1 mol % PAdDalPhosNi(o-tol)Cl, 25° C.) compound 4f was isolated as a yellow oil in 70% yield. A 1% ethyl acetate/hexanes eluent system was used for column chromatography on silica gel. $^1$H NMR (500 MHz, CDCl$_3$): δ 7.44-7.42 (m, 2H), 6.63-6.61 (m, 2H), 3.97 (br s, 1H), 3.19-3.15 (m, 2H), 1.69-1.64 (m, 2H), 1.47-1.42 (m, 2H), 1.37-1.32 (m, 8H), 0.93 (t, J=6.9 Hz, 3H); $^{13}C\{^1H\}$ NMR (125.8 MHz, CDCl$_3$): δ 151.1, 126.8 (d, $J_{CF}$=3.7 Hz), 126.4 (d, $J_{CF}$=269 Hz), 118.8 (d, $J_{CF}$=38.4 Hz), 112.0, 43.8, 32.1, 29.6, 29.5, 29.4, 27.4, 22.8, 14.3. Spectral data are in agreement with the literature. Following the protocol of GPF (25° C.) compound 4f was isolated as a yellow oil in 52% yield from the corresponding bromide (3 mol % PAdDalPhosNi(o-tol)Cl).

Synthesis of 4g.

Following the protocol of GPF: (0.50 mmol 4-chlorobenzonitrile, 0.55 mmol octylamine, 1 mol % PAdDalPhosNi(o-tol)Cl, 25° C.) compound 4g was isolated as a yellow solid in 80% yield. A 5% ethyl acetate/hexanes eluent system was used for column chromatography on silica gel. $^1$H NMR (500 MHz, CDCl$_3$): δ 7.46-7.44 (m, 2H), 6.58-6.56 (m, 2H), 4.18 (br s, 1H), 3.19-3.15 (m, 2H), 1.69-1.63 (m, 2H), 1.46-1.40 (m, 2H), 1.38-1.32 (m, 8H), 0.92 (t, J=6.9 Hz, 3H); $^{13}C\{^1H\}$ NMR (125.8 MHz, CDCl$_3$): δ 151.6, 133.9, 130.1, 120.8, 112.3, 98.7, 43.5, 32.0, 29.5, 29.4, 27.3, 22.9, 14.3. Spectral data are in agreement with the literature.

Synthesis of 4h.

Following the protocol of GPF: (0.50 mmol 2-chloro-1,4-dimethylbenzene, 0.55 mmol octylamine, 1 mol % PAdDalPhosNi(o-tol)Cl, 25° C.) compound 4h was isolated as a yellow oil in 75% yield. A 1% ethyl acetate/hexanes eluent system was used for column chromatography on silica gel. $^1$H NMR (500 MHz, CDCl$_3$): δ 6.98-6.96 (m, 1H), 6.51-6.48 (m, 2H), 3.43 (br s, 1H), 3.18 (t, J=6.6 Hz, 2H), 2.34 (s, 3H), 2.13 (s, 3H), 1.74-1.68 (m, 2H), 1.50-1.44 (m, 2H), 1.38-1:34 (m, 8H), 0.94 (t, J=7.1 Hz, 3H); $^{13}C\{^1H\}$ NMR (125.8 MHz, CDCl$_3$): δ 146.6, 136.9, 130.1, 118.9, 117.5, 110.8, 44.3, 32.6, 29.9, 29.7, 29.5, 27.4, 22.9, 21.9, 17.3, 14.4. Spectral data are in agreement with the literature.

Synthesis of 4i.

Following the protocol of GPF: (0.50 mmol 2'-bromo-2,6-dimethoxybiphenyl, 0.55 mmol octylamine, 5 mol % PAdDalPhosNi(o-tol)Cl, 25° C.) compound 4i was isolated as a light brown oil in 98% yield. A 0% to 5% ethyl acetate/hexanes eluent system was used for column chromatography on silica gel. $^1$H NMR (300 MHz, CDCl$_3$): δ 7.34 (t, J=8.4 Hz, 1H), 7.29-7.23 (m, 1H), 7.04-7.01 (m, 1H), 6.80-6.74. (m, 2H), 6.70 (s, 1H), 6.68 (s, 1H), 3.74 (s, 6H), 3.47 (br s, 1H), 3.14-3.09 (m, 2H), 1.56-1.46 (m, 2H), 1.34-1.27 (m, 10H), 0.92-0.88 (m, 3H); $^{13}C\{^1H\}$ NMR (75.5 MHz, CDCl$_3$): δ 158.4, 146.5, 131.2, 129.1, 128.5, 120.0, 116.4, 116.0, 110.5, 104.3, 56.0, 44.2, 31.9, 29.4, 29.3, 29.2, 27.0, 22.6, 14.1; HRMS m/z ESI$^+$ found 342.2428 [M+H]$^+$ calculated for $C_{22}H_{32}NO_2$ 342.2433.

Synthesis of 4j.

Following the protocol of GPG: (0.50 mmol 4-chloroquinaldine, 3.5 mmol methylamine, 5 mol % PAdDalPhosNi(o-tol)Cl, 25° C.) compound 4j was isolated as a white solid in 55% yield. A 2% trimethylamine, 38% hexane, 60% ethyl acetate eluent was used for column chromatography on silica gel. $^1$H NMR (500 MHz, CDCl$_3$): δ 7.97-7.95 (m, 1H), 7.70-7.68 (m, 1H), 7.65-7.61 (m, 1H), 7.42-7.38 (m, 1H), 6.38 (s, 1H), 5.00 (br s, 1H), 3.09 (d, J=5.0 Hz 3H), 2.67 (s, 3H); $^{13}C\{^1H\}$ NMR (125.8 MHz, CDCl$_3$): δ 159.9, 150.8, 148.4, 129.5, 129.2, 124.1, 119.2, 117.6, 99.0, 30.3, 26.0. Spectral data are in agreement with the literature. Following the protocol of GPD: (1.0 mmol 4-chloroquinaldine, 5.0 mmol methylammonium chloride, 1 mol % PAdDalPhosNi(o-tol)Cl, 140° C., 5 minutes) compound 4j was isolated as a white solid in 99% yield.

Synthesis of 4k.

Following the protocol of GPD: (1.0 mmol 4-chloroquinaldine, 5.0 mmol ethylammonium chloride, 1 mol % PAdDalPhosNi(o-tol)Cl, 140° C., 5 minutes) compound 4k was isolated as a white solid in 95% yield. $^1$H NMR (300 MHz, DMSO): δ 8.16-8.13 (m, 1H), 7.69-7.66 (m, 1H), 7.50-7.57 (m, 1H), 7.28-7.36 (m, 1H), 6.96-6.93 (m, J=5.1 Hz, 1H), 6.33 (s, 1H), 3.23-3.34 (m, 2H), 2.16 (s, 3H), 1.27 (t, J=7.1 Hz, 3H); $^{13}C\{^1H\}$ (75.5 MHz, DMSO): δ 158.6, 149.8, 148.0, 128.5, 128.2, 122.8, 121.4, 117.4, 97.9, 36.9, 25.2, 13.7; HRMS m/z ESI$^+$ found 187.1230 [M+H]$^+$ calculated for $C_{12}H_{15}N_2$ 187.1191.

Synthesis of 4l.

Following the protocol of GPF: (0.50 mmol 4-chloroquinaldine, 0.55 mmol sec-butylamine, 5 mol % PAdDalPhosNi(o-tol)Cl, 25° C.) compound 4l was isolated as a white solid in 65% yield. A 1% trimethylamine, 39% hexane, 60% ethyl acetate eluent was used for column chromatography on silica gel. $^1$H NMR (300 MHz, CDCl$_3$): δ 7.93-7.90 (m, 1H), 7.69-7.65 (m, 1H), 7.63-7.58 (m, 1H), 7.40-7.35 (m, 1H), 6.35 (br s, 1H), 4.74-4.72 (m, 1H), 3.74-3.60 (m, 1H), 2.64 (s, 3H), 1.83-1.59 (m, 2H), 1.34 (d, J=6.8 Hz, 3H), 1.04 (t, J=7.4 Hz, 3H); $^{13}C\{^1H\}$ NMR (125.8 MHz, CDCl$_3$): δ 159.8, 149.0, 148.8, 129.6, 129.2, 123.9, 119.1, 117.6, 99.4, 49.7, 29.7, 26.1, 20.1, 10.6; HRMS m/z ESI$^+$ found 215.1543 [M+H]$^+$ calculated for C$_{14}$H$_{19}$N$_2$ 215.1548.

Synthesis of 4m.

Following the protocol of GPG: (0.60 mmol 6-chloroquinoxaline, 4.2 mmol methylamine, 5 mol % PAdDalPhosNi(o-tol)Cl, 25° C., 0.085M concentration of aryl halide) compound 4m was isolated as a bright yellow solid in 81% yield. A 60% ethyl acetate/hexanes eluent system was used for column chromatography on silica gel. $^1$H NMR (500 MHz, CDCl$_3$): δ 8.68 (d, J=2.2 Hz, 1H), 8.54 (d, J=2.0 Hz, 1H), 7.88 (d, J=9.1 Hz, 1H), 7.17-7.15 (m, 1H), 7.00-6,99 (m, 1H), 4.31 (br s, 1H), 3.04 (d, J=5.2 Hz, 3H); $^{13}C\{^1H\}$ NMR (125.8 MHz, CDCl$_3$): δ 145.7, 145.0, 143.4, 140.4, 138.2, 130.1, 122.0, 103.3, 30.5. Spectral data are in agreement with the literature. Following the protocol of GPD: (1.0 mmol 6-chloroquinoxaline, 5.0 mmol methylammonium chloride 1 mol % PAdDalPhosNi(o-tol)Cl, 140° C., 15 minutes) compound 4m was isolated as a bright yellow solid in 99% yield.

Synthesis of 4n.

Following the protocol of GPG: (0.60 mmol 5-Chloro-1,3-benzodioxole, 4.2 mmol methylamine, 5 mol % PAdDalPhosNi(o-tol)Cl, 25° C.) compound 4n was isolated as a dark yellow oil in 80% yield. A 12% ethyl acetate/hexanes eluent system was used for column chromatography on silica gel. $^1$H NMR (500 MHz, CDCl$_3$): δ 6.72 (d, J=8.3 Hz, 1H), 6.29 (d, J=2.4 Hz, 1H), 6.09-6.07 (m, 1H), 5.89 (s, 2H), 3.51 (br s, 1H), 2.83 (m, 3H); $^{13}C\{^1H\}$ NMR (125.8 MHz, CDCl$_3$): δ 147.2, 145.3, 139.6, 108.6, 103.8, 100.5, 95.6, 31.7. Spectral data are in agreement with the literature. Following the protocol of GPF: (5 mol % PAdDalPhosNi(o-tol)Cl, 25° C.) compound 4n was isolated in 65% yield from the corresponding tosylate.

Synthesis of 4o.

Following the protocol of GPG: (0.24 mmol 4-chiorophenylboronic acid pinacol ester, 1.68 mmol methylamine, 3 mol % PAdDalPhosNi(o-tol)Cl, 25° C.) compound 4o was isolated as a clear colourless oil in 69% yield. A 10% ethyl acetate/hexanes eluent system was used for column chromatography on silica gel. $^1$H NMR (500 MHz, CDCl$_3$): δ 7.70-7.68 (m, 2H), 6.63-6.61 (m, 2H), 3.96 (br s, 1H), 2.89-2.88 (m, 3H), 1.37-1.36 (s, 12H); $^{13}C\{^1H\}$ NMR (125.8 MHz, CDCl$_3$): δ 152.0, 136.5, 111.7, 83.4, 30.5, 25.1; HRMS m/z ESI$^+$ found 234.1660 [M+H]$^+$ calculated for C$_{13}$H$_{21}$BNO$_2$ 234.1665.

Synthesis of 4p.

Following the protocol of GPD: (1 mmol 2-chloro-3-methylpyridine, 5 mmol ethylammonium chloride, 5 mol % PAdDalPhosNi(o-tol)Cl, 140° C., 20 minutes) compound 4p was isolated as a light yellow oil in 73% yield. A 20% ethyl acetate/hexanes eluent system was used for column chromatography on silica gel. $^1$H NMR (300 MHz, CDCl$_3$): δ 8.06-8.00 (m, 1H), 7.24-7.18 (m, 1H), 6.54-6.48 (m, 1H), 4.05 (br s, 1H) 3.58-3.46 (m, 2H), 2.08 (s, 3H), 1.29 (t, J=7.17, 3H); $^{13}C\{^1H\}$ NMR (75.5 MHz, CDCl$_3$): δ 156.9, 145.5, 136.6, 116.3, 112.3, 36.4, 16.9, 15.2; HRMS m/z ESI$^+$ found 173.1073 [M+H]$^+$ calculated for C$_8$H$_{13}$N$_2$ 173.1034.

Synthesis of 4q.

Following the protocol of GPF: (0.50 mmol 5-Chloro-2-methylbenzothiazole, 0.55 cyclohexylamine, 5 mol % PAdDalPhosNi(o-tol)Cl, 25° C.) compound 4q was isolated as a white solid in 98% yield. A 15% ethyl acetate/hexanes eluent system was used for column chromatography on silica gel. $^1$H NMR (500 MHz, CDCl$_3$): δ 7.55 (d, J=8.5 Hz, 1H), 7.12-7.18 (m, 1H), 6.70-6.68 (m, 1H), 3.66 (br s, 1H), 3.37-3.32 (m, 1H), 2.81 (s, 3H), 2.17-2.14 (m, 2H), 1.84-1.78 (m, 2H), 1.73-1.68 (m, 1H), 1.47-1.39 (m, 2H) 1.32-1.18 (m, 3H); $^{13}C\{^1H\}$ NMR (125.8 MHz, CDCl$_3$): δ 167.6, 155.4, 146.7, 123.8, 121.7, 114.1, 104.8, 52.4, 33.5, 26.2, 25.3, 20.3; HRMS m/z ESI$^+$ found 247.1263 [M+H]$^+$ calculated for C$_{14}$H$_{19}$N$_2$S 247.1269.

Synthesis of 4r.

Following the protocol of GPD: (1.0 mmol 5-chloro-2-methylbenzothiazole, 5.0 mmol ethylammonium chloride 2 mol % PAdDalPhosNi(o-tol)Cl, 140° C., 20 minutes) compound 4r was isolated as a brown solid in 52% yield. $^1$H NMR (500 MHz, CDCl$_3$): δ 7.58-7.57 (m, 1H), 7.22-7.21 (m, 1H), 6.80-6.75 (m, 1H), 3.25 (q, J=7.1 Hz, 2H), 2.21 (s, 3H), 1.33 (t, J=7.1 Hz, 3H); $^{13}C\{^1H\}$ (125.8 MHz, CDCl$_3$): δ 167.7, 155.1, 147.2, 124.5, 121.6, 113.8, 104.8, 39.3, 20.3, 14.8; HRMS m/z ESI$^+$ found [M+H]$^+$ calculated for C$_{10}$H$_{13}$N$_2$S 193.0755.

Synthesis of 4s.

Following the protocol of GPF: (0.50 mmol toluene-4-sulfonic acid 4-phenoxy-phenyl ester, 0.55 mmol racemic α-methylbenzylamine, 5 mol % PAdDalPhosNi(o-tol)Cl, 25° C.) compound 4s was isolated as a yellow oil in 70% yield. A 5% ethyl acetate/hexanes eluent system was used for column chromatography on silica gel. $^1$H NMR (500 MHz, CDCl$_3$): δ 7.43-7.41 (m, 2H), 7.39-7.36 (m, 2H), 7.31-7.26 (m, 3H), 7.04-7.01 (m, 2H), 6.94-6.92 (m, 2H), 6.86-6.84 (m, 2H), 6.56-6.53 (m, 2H), 4.51 (q, J=13.4 Hz, 1H), 4.04 (br s, 1H), 1.58 (d, J=6.7 Hz, 3H); $^{13}C\{^1H\}$ NMR (75.5 MHz, CDCl$_3$): δ 159.0, 147.9, 145.2, 144.0, 129.4, 128.7, 126.9, 125.9, 121.9, 121.0, 117.2, 114.2, 54.0, 25.1. Spectral data are consistent with the literature.

In an effort to evaluate whether such cross-couplings could be conducted with retention of stereochemistry within the α-methylbenzylamine substrate, the cross-coupling reaction was repeated using (S)-(−)-α-methylbenzylamine. In each case, the product 4s formed from the racemic and separately the enantiopure α-methylbenzylamine starting material was dissolved in CDCl$_3$ (0.6 mL) and treated with europium tris[-(heptafluoropropylhydroxymethylene)-(+)-camphorate] (ca. 8-10 mg); the $^1$H NMR spectrum of each mixture was then obtained.

The $^1$H NMR spectrum of 4s synthesized from racemic α-methylbenzylamine displayed two equal-intensity methyl resonances (doublets), in keeping with the racemic nature of the α-methylbenzylamine starting material. In contrast, only a single doublet methyl resonance was observed in the case of 4s prepared from (S)-(−)-α-methylbenzylamine under analogous conditions. These observations provide qualitative confirmation that racemization of the (S)-(−)-α-methylbenzylamine starting material under cross-coupling conditions leading to 4s does not occur.

Synthesis of 4t.

Following the protocol of GPF: (0.50 mmol chlorobenzene, 5.5 mmol 4-methyl-1-piperazinamine, 3 mol % PAdDalPhosNi(o-tol)Cl, 25° C.) compound 4t was isolated as a white solid in 76% yield. A 1% triethylamine, 2% methanol, 97% ethyl acetate eluent system was used for column chromatography on silica gel. $^1$H NMR (500 MHz, CDCl$_3$): δ 7.24-7.21 (m, 2H), 6.94-6.92 (m, 2H), 6.84-6.80 (m, 1H), 4.38 (br s, 1H), 2.82 (s, 4H), 2.60 (s, 4H), 2.37 (s, 3H); $^{13}C\{^1H\}$ NMR (125.8 MHz, CDCl$_3$): δ 147.2, 129.4, 119.7, 113.9, 56.0, 55.4.3, 46.0. Spectral data are in agreement with the literature. Following the protocol of GPF: (3 mol %

PAdDalPhosNi(o-tol)Cl, 25° C.) compound 4t was isolated as a dark yellow oil in 76% yield from the corresponding tosylate.

Synthesis of 4u.

Following the protocol of GPF: (0.50 mmol 5-chlorobenzothiophene, 0.55 mmol 3-(trifluoromethyl)aniline, 3 mol % PAdDalPhosNi(o-tol)Cl, 25° C.) compound 4u was isolated as a green crystalline solid in 94% yield. A 100% hexane to 5% ethyl acetate/hexanes eluent system was used for column chromatography on silica gel. $^1$H NMR (500 MHz, CDCl$_3$): δ 7.86 (d, J=8.6 Hz, 1H), 7.62-7.61 (m, 1H), 7.52 (d, J=5.4 Hz, 1H), 7.39-7.36 (m, 1H), 7.29-7.28 (m, 2H), 7.23-7.21 (m, 1H), 7.19-7.15 (m, 2H), 5.90 (br s, 1H); $^{13}$C{$^1$H} NMR (125.8 MHz, CDCl$_3$): δ 145.0, 140.8, 138.6, 134.4, 132.0, 131.7, 129.9, 127.8, 123.5, 123.4, 119.2, 118.8, 116.6, 114.1, 112.7 (q, J$_{CF}$=30.4 Hz); HRMS m/z ESI$^+$ found 294.0559 [M+H]$^+$ calculated for C$_{15}$H$_{11}$F$_3$NS 294.0564.

Synthesis of 4v.

Following the protocol of GPF: (0.50 mmol 3-chlorobenzotrifluoride, 0.55 mmol 4-methoxyaniline, 3 mol % PAdDalPhosNi(o-tol)Cl, 25° C.) compound 4v was isolated as a dark oil in 97% yield. A 10% ethyl acetate/hexanes eluent system was used for column chromatography on silica gel. $^1$H NMR (500 MHz, CDCl$_3$): δ 7.33-7.32 (m, 1H), 7.14-7.11 (m, 3H), 7.08-7.06 (m, 1H), 7.05-7.03 (m, 1H), 6.95-6.93 (m, 2H), 5.65 (br s, 1H), 3.86 (s, 3H); $^{13}$C{$^1$H} NMR (125.8 MHz, CDCl$_3$): δ 156.5, 146.3, 134.6, 130.0, 123.8, 118.1, 115.9, 115.2, 111.6, 55.8. Spectral data are in agreement with the literature.

Synthesis of 4w.

Following the protocol of GPF: (0.50 mmol 2-chloro-4,6-dimethoxypyrimidine, 0.55 mmol phenethylamine, 3 mol % PAdDalPhosNi(o-tol)Cl, 25° C.) compound 4w was isolated as a white solid in 67% yield. A 5% ethyl acetate/hexanes eluent system was used for column chromatography on silica gel. $^1$H NMR (500 MHz, CDCl$_3$): δ 7.36-7.30 (m, 2H), 7.27-7.21 (m, 2H), 5.43 (s, 1H), 4.96 (br s, 1H), 3.87 (s, 6H), 3.72-3.65 (m, 2H), 2.93 (t, J=12.0 Hz, 2H); $^{13}$C{$^1$H} NMR (125.8 MHz, CDCl$_3$): δ 172.2, 161.7, 139.4, 128.8, 128.5, 78.7, 53.5, 42.8, 36.0; HRMS m/z ESI$^+$ found 260.1394 [M+H]$^+$ calculated for C$_{14}$H$_{18}$N$_3$O$_2$ 260.1399.

Synthesis of 4x.

Following the protocol of GPF: (0.50 mmol 1-(4-chlorophenyl)-1H-pyrrole, 0.55 mmol furfurylamine, 1 mol % PAdDalPhosNi(o-tol)Cl, 25° C.) compound 4x was isolated as white solid in 85% yield. A 100% hexane to 5% ethyl acetate/hexanes eluent system was used for column chromatography on silica gel. $^1$H NMR (500 MHz, CDCl$_3$): δ 7.42-7.41 (m, 1H), 7.27-7.24 (m, 2H), 7.01-6.99 (m, 2H), 6.76-6.73 (m, 2H), 6.38-6.37 (m, 1H), 6.34-6.33 (m, 2H), 6.30-6.29 (m, 1H), 4.38 (s, 2H), 4.11 (br s, 1H); $^{13}$C{$^1$H} NMR (125.8 MHz, CDCl$_3$): δ 152.7, 146.1, 142.3, 132.8, 122.7, 120.1, 114.0, 110.7, 109.7, 107.3, 41.9; HRMS m/z ESI$^+$ found 239.1179 [M+H]$^+$ calculated for C$_{15}$H$_{15}$N$_2$O 239.1184. Following the protocol of GPF: (3 mol % PAdDalPhosNi(o-tol)Cl) compound 4x was isolated as a white solid in 66% yield from the corresponding tosylate. Following the protocol of GPH: (5 mol % PAdDalPhosNi(o-tol)Cl) compound 4x was isolated as a white solid in 74% yield from the corresponding mesylate.

Synthesis of 4y.

Following the protocol of GPF: (0.50 mmol 4-benzophenone, 0.55 mmol tetrahydrofurfurylamine, 3 mol % PAdDalPhosNi(o-tol)Cl, 25° C.) compound 4y was isolated as a yellow oil in 97% yield. A 10% ethyl acetate/hexanes eluent system was used for column chromatography on silica gel. $^1$H NMR (500 MHz, CDCl$_3$): δ 7.78-7.74 (m, 4H), 7.57-7.54 (m, 1H), 7.50-7.47 (m, 2H), 6.65-6.63 (m, 2H), 4.64 (br s, 1H), 4.20-4.17 (m, 1H), 3.97-3.92 (m, 1H), 3.86-3.82 (m, 1H), 3.41-3.39 (m, 1H), 3.23-3.18 (m, 1H), 2.13-2.06 (m, 1H), 2.01-1.95 (m, 2H), 1.73-1.66 (m, 1H); $^{13}$C{$^1$H} NMR (125.8 MHz, CDCl$_3$): δ 152.2, 139.2, 132.9, 131.1, 129.4, 128.0, 126.2, 111.8, 68.4, 47.3, 29.1, 25.8; HRMS m/z ESI$^+$ found 304.1308 [M+Na]$^+$ calculated for C$_{18}$H$_{19}$NNaO$_2$ 304.1313.

Synthesis of 4z.

Following the protocol of GPF: (0.50 mmol 3-bromo-4-methylbenzonitrile, 0.55 mmol 2-thiophenemethylamine, 1 mol % PAdDalPhosNi(o-tol)Cl, 25° C.) compound 4z was isolated as a yellow solid in 94% yield. An 8% ethyl acetate/hexanes eluent system was used for column chromatography on silica gel. $^1$H NMR (300 MHz, CDCl$_3$): δ 7.29-7.27 (m, 1H), 7.16-7.13 (m, 1H), 7.07-7.05 (m, 1H), 7.03-6.98 (m, 2H), 6.88-6.87 (m, 1H), 4.58 (d, J=5.6 Hz, 2H), 2.22 (s, 3H); $^{13}$C{$^1$H} NMR (125.8 MHz, CDCl$_3$): δ 146.1, 141.7, 130.9, 127.9, 127.4, 125.8, 125.3, 121.8, 120.1, 112.7, 110.9, 43.4, 18.0; HRMS m/z ESI$^+$ found 251.0613 [M+Na]$^+$ calculated for C$_{13}$H$_{12}$N$_2$NaS 251.0619.

Synthesis of 4aa.

Following the protocol of GPH: (0.50 mmol methanesulfonic acid 2,5-dimethyl-phenyl ester, 0.55 mmol 2-thiophenemethylamine, 5 mol % PAdDalPhosNi(o-tol)Cl) compound 4aa was isolated as a yellow oil in 87% yield. A 5% ethyl acetate/hexanes eluent system was used for column chromatography on silica gel. $^1$H NMR (500 MHz, CDCl$_3$): δ 7.29-7.28 (m, 1H), 7.10-7.08 (m, 1H), 7.04-7.01 (m, 2H), 6.59-6.58 (m, 2H), 4.60 (s, 2H), 3.86 (br s, 1H), 2.34 (s, 3H), 2.17 (s, 3H); $_{13}$C{$^1$H} NMR (125.8 MHz, CDCl$_3$): δ 145.7, 143.3, 137.0, 130.2, 127.1, 125.3, 124.8, 119.5, 118.5, 111.3, 43.7, 21.8, 17.3; HRMS m/z ESI$^+$ found 218.0998 [M+H]$^+$ calculated for C$_{13}$H$_{16}$NS 218.1003.

Synthesis of 4ab.

Following the protocol of GPF: (0.50 mmol toluene-4-sulfonic acid quinolin-8-yl ester, 0.55 mmol benzylamine, 3 mol % PAdDalPhosNi(o-tol)Cl, 25° C.) compound 4ab was isolated as a yellow oil in 60% yield. A 5% ethyl acetate/hexanes eluent system was used for column chromatography on silica gel. $^1$H NMR (500 MHz, CDCl$_3$): δ 8.77-8.76 (m, 1H), 8.12-8.10 (m, 1H), 7.50-7.48 (m, 2H), 7.43-7.30 (m, 5H), 7.11-7.10 (m, 1H), 6.70-6.69 (m, 1H), 6.55 (br s, 1H), 4.61-4.60 (m, 2H); $^{13}$C{$^1$H} NMR (75.5 MHz, CDCl$_3$): δ 159.8, 149.0, 148.8, 129.6, 129.2, 123.9, 119.1, 117.6, 99.4, 49.7, 29.7, 26.1, 20.1, 10.6. Spectral data are consistent with the literature. Following the protocol of GPH: (3 mol % PAdDalPhosNi(o-tol)Cl) compound 4ab was isolated as a yellow oil in 55% yield from the corresponding mesylate.

Synthesis of 4ac.

Following the protocol of GPF: (0.12 mmol 2-chlorobenzonitrile, 0.132 mmol allylamine, 5 mol % PAdDalPhosNi(o-tol)Cl, 60° C.) compound 4ac was isolated as a yellow oil in 70% yield. A 30% CH$_2$Cl$_2$/hexanes eluent system was used for column chromatography on silica gel. $^1$H NMR (500 MHz, CDCl$_3$): δ 7.44-7.39 (m, 2H), 6.74-6.68 (m, 2H), 5.99-5.92 (m, 1H), 5.36-5.32 (m, 1H), 5.27-5.25 (m, 1H), 4.77 (br s, 1H); 3.92-3.90 (m, 2H); $^{13}$C{$^1$H} NMR (125.8 MHz, CDCl$_3$): δ 150.3, 134.4, 134.0, 132.9, 118.1, 117.3, 116.9, 111.2, 96.1, 46.2. Spectral data are consistent with the literature.

Synthesis of 4ad.

Following the protocol of GPF: (0.50 mmol 2-chloro-6-methoxypyridine, 0.55 mmol 4-(aminomethyl)piperidine, 3 mol % PAdDalPhosNi(o-tol)Cl, 25° C.) compound 4ad was isolated as a clear solid in 78% yield. The reaction mixture was cooled and filtered through a short plug of alumina and washed with ethyl acetate (50 mL) and the product was collected with methanol (40 mL). After concentrating the methanol solution under reduced pressure, the crude product was purified by washing with cold hexanes (3×5 mL). $^1$H NMR (300 MHz, CDCl$_3$): δ 7.34 (t, J=8.0 Hz 1H), 6.04 (d, J=7.8 Hz 1H), 5.95 (d, J=8.0 Hz 1H), 4.53-4.49 (m, 1H), 4.04 (s, 2H), 3.85 (s, 3H), 3.39-3.35 (m, 2H), 3.26-3.21 (m, 2H), 2.81-2.72 (m, 2H), 1.94-1.87 (m, 2H), 1.59-1.45 (m, 2H); $^{13}$C{$^1$H} NMR (125.8 MHz, CDCl$_3$): δ 163.9, 157.9, 140.3, 98.1, 97.5, 53.4, 47.6, 45.0, 35.6, 28.6; HRMS m/z ESI$^+$ found 222.1601 [M+H]$^+$ calculated for C$_{12}$H$_{20}$N$_3$O 222.1606.

Synthesis of 4ae.

Following the protocol of GPF: (0.50 mmol chlorobenzene, 0.55 mmol N-phenylethylenediamine, 3 mol % PAdDalPhosNi(o-tol)Cl, 25° C.) compound 4ae was isolated as a white solid in 96% yield. The reaction mixture was cooled and filtered through a short plug of silica on Celite and washed with dichloromethane (40 mL). After concentrating the so-formed mixture under reduced pressure, the crude product was purified by washing with cold hexanes (3×5 mL). $^1$H NMR (300 MHz, CDCl$_3$): δ 7.26-7.21 (m, 4H), 6.80-6.75 (m, 2H), 6.70-6.68 (m, 4H), 3.88 (s, 2H), 3.43 (s, 4H); $^{13}$C{$^1$H} NMR (125.8 MHz, CDCl$_3$): δ 148.0, 129.3, 117.8, 113.0, 43.3. Spectral data are consistent with the literature. Following the protocol of GPF: (3 mol % PAdDalPhosNi(o-tol)Cl) compound 4ae was isolated as a white solid in 98% yield from the corresponding tosylate.

Synthesis of 4af.

Following the protocol of GPF: (0.50 mmol 3-chloropyridine, 0.55 mmol N-phenylethylenediamine, 3 mol % PAdDalPhosNi(o-tol)Cl, 25° C.) compound 4af was isolated as a pale yellow oil in 65% yield. The reaction mixture was cooled and filtered through a short plug of silica on Celite and washed with dichloromethane (40 mL). After concentrating the so-formed mixture under reduced pressure, the crude product was purified by washing with cold hexanes (3×5 mL). $^1$H NMR (300 MHz, CDCl$_3$): δ 8.10-8.08 (m, 1H), 8.03-8.01 (m, 1H), 7.28-7.19 (m, 2H), 7.14-7.09 (m, 1H), 6.94-6.91 (m, 1H), 6.80-6.75 (m, 1H) 6.70-6.68 (m, 2H), 3.99 (br s, 1H), 3.88 (br s, 1H), 3.44 (s, 4H); $^{13}$C{$^1$H} NMR (125.8 MHz, CDCl$_3$): δ 147.8, 144.0, 139.2, 136.3, 129.4, 123.7, 118.7, 118.0, 113.1, 43.1, 42.9. Spectral data are consistent with the literature.

Synthesis of 4ag.

Following the protocol of GPI: (0.2 mmol 4-chloroanisole, 0.2 mmol carbazole, 10 mol % PAdDalPhosNi(o-tol)Cl (P1)) compound 4ag was isolated as a yellow oil in 58% yield. Purified by preparatory TLC using 10:1 hexanes:ethyl acetate. $^1$H NMR (300 MHz, CDCl$_3$): δ 8.15-8.13 (m, 2H), 7.48-7.46 (m, 1H), 7.45-7.43(m, 1H) 7.41-7.40 (m, 1H), 7.38-7.37 (m, 1H), 7.34-7.33 (m, 1H), 7.31-7.29 (m, 1H), 7.27-7.24 (m, 2H), 7.14-7.09 (m, 2), 3.92 (s, 3H); $^{13}$C{$^1$H} NMR (125.8 MHz, CDCl$_3$): δ 159.0, 141.5, 130.4, 128.7, 125.9, 123.2, 120.3, 119.7, 115.1, 109.8, 55.7. Spectral data are in agreement with the literature.

Synthesis of 4ah.

Following the protocol of GPI: (0.2 mmol 4-chlorobenzonitrile, 0.2 mmol carbazole 10 mol % PAdDalPhosNi(o-tol)Cl (P1)) compound 4ah was isolated as a yellow oil in 63% yield. Purified by preparatory TLC using 10:1 hexanes: ethyl acetate. $^1$H NMR (500 MHz, CDCl$_3$): δ 8.15 (d, J=7.8 Hz, 2H), 7.91 (d, J=8.4 Hz, 2H), 7.75 (d, J=8.4 Hz, 2H), 7.45-7.43 (m, 4H), 7.35-7.32 (m, 2H); $^{13}$C{$^1$H} NMR (125.8 MHz, CDCl$_3$): δ 142.8, 140.0, 133.9, 127.2, 126.4, 124.1, 121.0, 120.6, 118.2, 110.6, 109.5. Spectral data are in agreement with the literature.

Synthesis of 4ai.

Following the protocol of GPI: (0.2 mmol 4-chloroanisole, 0.2 mmol indole, 10 mol % PAdDalPhosNi(o-tol)Cl (P1)) compound 4ai was isolated as a yellow oil in 68% yield. Purified by preparatory TLC using 10:1 hexanes:ethyl acetate. $^1$H NMR (300 MHz, CDCl$_3$): δ 7.71 (d, J=8.7 Hz, 1H), 7.50-7.40 (m, 3H), 7.30-7.29 (m, 1H), 7.21-7.17 (m, 2H), 7.09-7.03 (m, 2H), 6.68-67 (m, 1H), 3.90 (s, 3H); $^{13}$C{$^1$H} NMR (125.8 MHz, CDCl$_3$): δ 158.5, 136.6, 133.1, 129.2, 128.5, 126.2, 122.4, 121.2, 120.3, 115.0, 110.6, 103.1, 55.8. Spectral data are in agreement with the literature.

Synthesis of 4aj.

Following the protocol of GPI: (0.2 mmol 4-chlorobenzonitrile, 0.2 mmol indole, 10 mol % PAdDalPhosNi(o-tol) Cl (P1)) compound 4aj was isolated as a yellow oil in 56% yield. Purified by preparatory TLC using 10:1 hexanes: diisopropylamine. $^1$H NMR (300 MHz, CDCl$_3$): δ 8.41-8.38 (m, 1H), 8.08-8.04 (m, 2H), 8.00-7.97 (m, 1H), 7.83-7.79 (m, 2H), 7.57 (d, J=3.8 Hz, 1H), 7.22-7.17 (m, 1H), 6.71 (d, J=3.8 Hz, 1H); $^{13}$C{$^1$H} NMR (125.8 MHz, CDCl$_3$): δ 147.6, 143.9, 142.2, 133.4, 129.5, 126.4, 123.1, 122.2, 118.7, 117.6, 108.9, 103.7. HRMS m/z ESI$^+$ found: 220.0865 [M+H]$^+$ calculated for C$_{14}$H$_{10}$N$_3$ 220.0869.

In the preceding description, for purposes of explanation, numerous details are set forth in order to provide a thorough understanding of the examples. However, it will be apparent to one skilled in the art that these specific details are not required. Accordingly, what has been described is merely illustrative of the application of the described examples and numerous modifications and variations are possible in light of the above teachings.

Since the above description provides examples, it will be appreciated that modifications and variations can be effected to the particular examples by those of skill in the art. Accordingly, the scope of the claims should not be limited by the particular examples set forth herein, but should be construed in a manner consistent with the specification as a whole.

What is claimed is:

1. A compound having a chemical formula according to Formula (I)

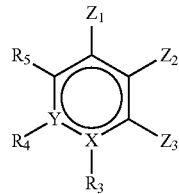

Formula (I)

wherein:

X is C, N, O or S;

Y is C or is absent;

R$_5$ is: H, alkyl, alkoxy, thioalkoxv, carboxy, carboxyalkyl, or halogen;

when X is C, then Y is C, and R$_3$ and R$_4$ are, independently: H, alkyl, alkoxy, thioalkoxy, carboxy, carboxyalkyl, or halogen;

when X is N and when Y is a C, then R$_3$ is absent and R$_4$ is: H, alkyl, alkoxy, thioalkoxy, carboxy, carboxyalkyl, or halogen;

when X is N and when Y is absent, then R$_4$ is absent and Formula (I) is

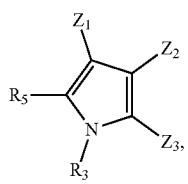

where $R_3$ is: H, aryl, or alkyl;

when X is O, then Y is absent, $R_3$ and $R_4$ are both absent, and Formula (I) is

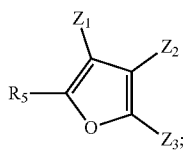

and when X is S, then Y is absent, $R_3$ and $R_4$ are both absent, and Formula (I) is

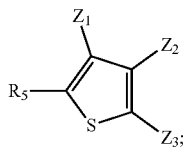

and one of $Z_1$, $Z_2$ and $Z_3$ is

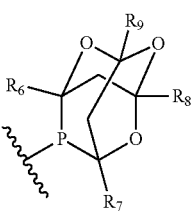

and:

when $Z_1$ is

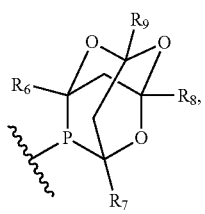

then $Z_2$ is $P(AR_1)(A'R_2)$, and $Z_3$ is H, alkyl, alkoxy, thioalkoxy, carboxy, carboxyalkyl, or halogen;

when $Z_2$ is

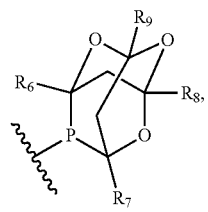

then one of $Z_1$ and $Z_3$ is $P(AR_1)(A'R_2)$, and the other of $Z_1$ and $Z_3$ is H, alkyl, alkoxy, thioalkoxy, carboxy, carboxyalkyl, or halogen; and when $Z_3$ is

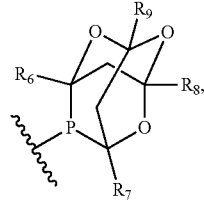

then $Z_2$ is $P(AR_1)(A'R_2)$, and $Z_1$ is H, alkyl, alkoxy, thioalkoxy, carboxy, carboxyalkyl, or halogen;

wherein:

A and A' are, independently: O or a bond;

$R_1$ and $R_2$ are, independently: aryl, alkyl, or cycloalkyl, where the aryl, alkyl or cycloalkyl is substituted or unsubstituted; and $R_6$, $R_7$, $R_8$ and $R_9$ are, independently, alkyl.

2. The compound according to claim 1, wherein $Z_2$ is

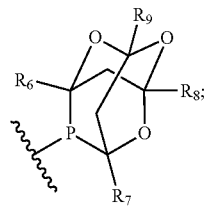

and $Z_3$ is $P(AR_1)(A'R_2)$.

3. The compound according to claim 2, wherein:

X and Y are both C;

A and A' are bonds; and $R_6$, $R_7$, $R_8$ and $R_9$ are methyl.

4. The compound according to claim 3, wherein $R_3$, $R_4$, $R_5$, and $Z_1$ are H.

5. The compound according to claim 2, wherein:

X is N, and Y is C; and

A and A' are both bonds.

6. The compound according to claim 5, wherein $R_3$, $R_4$, $R_5$, and $Z_1$ are H.

7. The compound according to claim 2, wherein:
Y is absent;
R$_4$ is absent; and
Formula (I) is

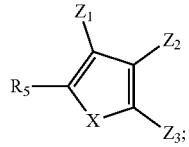

and wherein
X is N, O or S; and
A and A' are both bonds.

8. The compound according to claim 7, wherein R$_3$, R$_5$ and Z$_1$ are H.

9. The compound according to claim 1, wherein R$_5$ and Z$_1$ are both H.

10. The compound according to claim 1, wherein A and A' are both bonds.

11. The compound according to claim 1, wherein R$_6$, R$_7$, R$_8$, and R$_9$ are methyl.

12. The compound according to claim 1, wherein R$_1$ and R$_2$ are, independently:

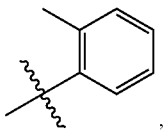 [SMILES: *c1ccccc1C]

phenyl, isopropyl, cyclohexyl, tert-butyl, or 1-adamantyl.

13. The compound according to claim 1, wherein:
X and Y are C;
Z$_1$ is H;
Z$_2$ is

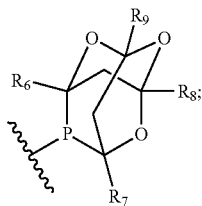

Z$_3$ is P(AR$_1$)(A'R$_2$);
A and A' are bonds;
R$_1$ and R$_2$ are

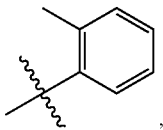

phenyl, isopropyl, cyclohexyl, tert-butyl, or 1-adamantyl;
R$_3$, R$_4$, and R$_5$ are H; and
R$_6$, R$_7$, R$_8$, and R$_9$ are methyl.

14. The compound according to claim 13, wherein R$_1$ and R$_2$ are

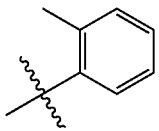

15. The compound according to claim 1, wherein: X is S; Y is absent; R$_3$ and R$_4$ are absent; R$_5$ and Z$_1$ are H; and Formula (I) is

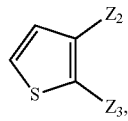

wherein Z$_2$ is P(AR$_1$)(A'R$_2$) where A and A' are bonds and R$_1$ and R$_2$ are

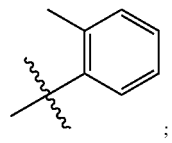 [SMILES: *c1ccccc1C]

and Z$_3$ is

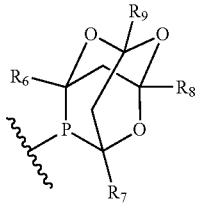

where R$_6$-R$_9$ are methyl.

16. The compound according to claim 1, wherein: X is N; Y is a C; R$_3$ is absent; R$_4$ and R$_5$ are H; Z$_1$ is H; Z$_2$ is P(AR$_1$)(A'R$_2$) where A and A' are bonds and R$_1$ and R$_2$ are

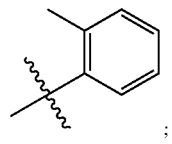 [SMILES: *c1ccccc1C]

and Z$_3$ is

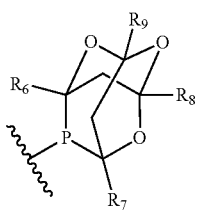

where R$_6$-R$_9$ are methyl.

17. A pre-catalyst comprising nickel complexed to a compound according to claim 1.

18. The pre-catalyst according to claim 17, wherein the nickel is additionally complexed to one or two chlorides.

19. The pre-catalyst according to claim 17, wherein the nickel is additionally complexed to one chloride and one

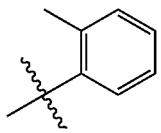

group.

20. The pre-catalyst according to claim 17, wherein the nickel is additionally complexed to two

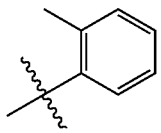 [SMILES: *c1ccccc1C]

groups.

21. The pre-catalyst according to claim 17, wherein the nickel is additionally complexed to two naphthyl groups.

* * * * *